(12) United States Patent
Egan et al.

(10) Patent No.: US 7,888,116 B2
(45) Date of Patent: Feb. 15, 2011

(54) USES OF NOTCH RECEPTORS, NOTCH LIGANDS, AND NOTCH MODULATORS IN METHODS RELATED TO METABOLIC DISEASES

(75) Inventors: Josephine M. Egan, Baltimore, MD (US); Máire E. Doyle, Gainesville, FL (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 265 days.

(21) Appl. No.: 11/658,189

(22) PCT Filed: Jul. 22, 2005

(86) PCT No.: PCT/US2005/026267
§ 371 (c)(1),
(2), (4) Date: Aug. 18, 2008

(87) PCT Pub. No.: WO2006/023209
PCT Pub. Date: Mar. 2, 2006

(65) Prior Publication Data
US 2008/0299088 A1 Dec. 4, 2008

(51) Int. Cl.
*C12N 5/00* (2006.01)
(52) U.S. Cl. .................................................... 435/325
(58) Field of Classification Search ........................ None
See application file for complete search history.

(56) References Cited

U.S. PATENT DOCUMENTS 6,703,221 B1  3/2004  Chan et al.

OTHER PUBLICATIONS

Weijzen et al. "The Notch ligand jagged-1 is able to induce maturation of monocyte-derived human dendritic cells", The J of Immunology, 2002, 169:4273-4278.*
Heremans, Y., et al., "Recapitulation of embryonic neuroendocrine differentiation in adult human pancreatic duct cells expressing neurogenin 3", The Journal of Cell Biology, vol. 159, No. 2, Oct. 28, 2002, pp. 303-311.
Hald, et al., "Activated Notch1 prevents differentiation of pancreatic acinar cells and attenuate endocrine development", Developmental Biology, Aug. 15, 2003, vol. 206, No. 2, pp. 426-437.
Apelqvist, A., et al., "Notch signaling controls pancreatic cell differentiation", Nature, Aug. 26, 1999, vol. 400, No. 6747, pp. 877-881.
Artavanis-Tsakonas et al., "Notch signaling: Cell fate control and signal integration in development," Science 284:770-776 (1999).
Bonner-Weir, "Life and death of the pancreatic beta cells," Trends Endocrinol. Metab. 11:375-378 (2000).
Conboy et al., "Notch-mediated restoration of regenerative potential to aged muscle," Science 302:1575-1577 (2003).

Doyle et al., "Glucagon-like peptide-1," Rec. Prog. Hormone Res. 56:377-99 (2001).
Drucker et al., "Glucagon-like peptide I stimulates insulin gene expression and increases cyclic AMP levels in a rat islet cell line," Proc. Nat. Acad. Sci. USA 84:3434-3438 (1987).
Drucker, "Glucagon-like peptide-1 and the islet β-cell; augmentation of cell proliferation and inhibition of apoptosis," Endocrinology 144:5145-5148 (2003).
Fajans et al., "Molecular mechanisms and clinical pathophysiology of maturity-onset diabetes of the young," N. Eng. J. Med. 13:971-980 (2001).
Fleenor et al., "Prolactin induction of insulin gene transcription: Roles of glucose and signal transducer and activator of transcription 5," Endocrinology 142:2805-2810 (2001).
Fortini, "γ-Secretase-mediated proteolysis in cell-surface-receptor signalling," Nature Reviews 3:673-684 (2002).
Habener, "The role of pancreatic duodenum homeobox protein-1 in the development of diabetes mellitus," Drug News Perspect. 15:491-497 (2002).
Hart et al., "Fgf10 maintains notch activation, stimulates proliferation, and blocks differentiation of pancreatic epithelial cells," Dev. Dyn. 228: 185-193 (2003).
He et al., "Interaction of filamin A with insulin receptor alters insulin-dependent activation of the mitogen-activated protein kinase pathway," J. Biol. Chem. 278:27096-27104 (2003).
Hennige et al., "Upregulation of insulin receptor substrate-2 in pancreatic β-cells prevents diabetes," J. Clin. Invest. 112:1521-1532 (2003).
Holst et al., "Therapy of type 2 diabetes mellitus based on the actions of glucagon-like peptide-1," Diabetes Metab. Res. Rev. 18:430-441 (2002).
Jang et al., "Notch-1 regulates cell death independently of differentiation in murine erythroleukemia cells through multiple apoptosis and cell cycle pathways," J. Cell. Physiol. 199:418-33 (2004).
Jarriault et al., "Delta-1 activation of notch-1 signaling results in HES-1 transactivation,"Mol. Cell. Biol. 18(12):7423-7431 (1998).
Jensen et al., "Control of endodermal endocrine development by Hes-1," Nat. Genetics 24:36-44 (2000).
Jensen, "Gene regulatory factors in pancreatic development," Dev. Dyn. 229:176-200 (2004).
Jhala et al. "cAMP promotes pancreatic β-cell survival via CREB-mediated induction of IRS2," Genes & Dev. 17:1575-1580 (2003).
Kaneta et al., "A role for Pref-1 and HES-1 in thymocyte development," J. Immunol. 164:256-264 (2000).

(Continued)

Primary Examiner—Karen Cochrane Carlson
Assistant Examiner—Bin Shen
(74) Attorney, Agent, or Firm—Edwards Angell Palmer & Dodge LLP

(57) ABSTRACT

Disclosed are methods for identifying and isolating a precursor cell. Also, disclosed are methods of increasing insulin synthesis from a pancreatic B-cell. Further, disclosed are methods of improving pancreatic B-cell function. Still further, disclosed are methods of preventing or delaying the onset of a metabolic disease, methods of treating or preventing a metabolic disease in a subject, and to compositions for treating or preventing a metabolic disease in a subject in need of such treatment or prevention.

20 Claims, 8 Drawing Sheets

OTHER PUBLICATIONS

Karlstrom et al., "A sensitive and quantitative assay for measuring cleavage of presenilin substrates," *J. Biol. Chem.* 277:6763-6766 (2002).

Kitamura et al., "The forkhead transcription factor Foxo1 links insulin signaling to Pdx1 regulation of pancreatic beta cell growth," *J Clin. Invest.* 110:1839-1847 (2002).

Lammert et al., "Notch gene expression during pancreatic organogenesis," *Mech. Dev.* 94(1-2):199-203 (2000).

Lee et al., "Regulation of the pancreatic pro-endocrine gene neurogenin 3," *Diabetes* 50(5):928-936 (2001).

Lester et al., "Anchoring of protein kinase A facilitates hormone-mediated insulin secretion," *Proc. Natl. Acad. Sci .USA* 94:14942-14947 (1997).

Li et al., "Photoactivated gamma-secretase inhibitors directed to the active site covalently label presenilin 1," *Nature* 405:689-694 (2000).

Ling et al, "Glucagon-like peptide 1 receptor signalling influences topography of islet cells in mice," *Virchows Arch.* 438:382-387 (2001).

Miyamoto et al., "Notch mediates TGF β-induced changes in epithelial differentiation during pancreatic tumorigenesis," *Cancer Cell* 3:565-576 (2003).

Mosley et al., "Glucose regulation of insulin gene expression requires the recruitment of p300 by the beta-cell specific transcription factor pdx-1," *Mol. Endocrinol.* May 27, 2004.

Nam et al., "Structural requirements for assembly of the CSL intracellular Notch1 Mastermind-like 1 transcriptional activation complex," *J. Biol. Chem.* 278:21232-21239 (2003).

Nickoloff et al., "Jagged-1 mediated activation of Notch signaling induces complete maturation of human keratinocytes through NF-kappaB and PPARgamma," *Cell Death Differ.* 9:842-855 (2002).

Nijjar et al., "Notch receptor expression in adult human liver: A possible role in bile duct formation and hepatic neovascularization," *Hepatology* 34:1184-1192 (2001).

Nijjar et al., "Altered notch ligand expression in human liver disease," *Am. J. Pathol.* 160:1695-1703 (2002).

Perfetti et al., "Glucagon-like peptide-1 induces cell proliferation and pancreatic-duodenum homeobox-1 expression and increases endocrine cell mass in the pancreas of old, glucose-intolerant rats," *Endocrinology* 141:4600-4605 (2000).

Petroff et al., "Glucagon-like peptide-1 increases cAMP but fails to augment contraction in adult rat cardiac myocytes," *Cir. Res.* 89:452-445 (2001).

Rand et al., "Calcium depletion dissociates and activates heterodimeric Notch receptors," *Mol. Cell Biol.* 20:1825-1835 (2000).

Satoh et al., "Roles for c-Myc in self renewal of hematopoietic stem cells," *J. Biol. Chem.* 279:24986-24993 (2004).

Schroeter et al., "Notch-1 signalling requires ligand-induced proteolytic release of intracellular domain," *Nature* 393:382-386 (1998).

Scrocchi et al., "Glucose intolerance but normal satiety in mice with a null mutation in the glucagon-like peptide 1 receptor gene," *Nat. Med.* 2: 1254-1258 (1996).

Sharma et al., "Novel pancreatic precursor cell lines for studying β-cell differentiation," *Diabetes* 50(1):S42-S43 (2001).

Shearman et al. "L-685,458, an aspartyl protease transition state mimic, is a potent inhibitor of amyloid β-protein γ-secretase activity," *Biochem.* 39:8698-8704 (2000).

Stanojevic et al., "Pancreas duodenum homeobox-1 transcriptional activation requires interactions with p300," *Endocrinology* 145:2918-2928 (2004).

Stoffers et al., "Early-onset type-II diabetes mellitus (MODY4) linked to IPF1," *Nature Genetics* 17:138-139 (1997).

Takahashi et al., "Post-priming actions of ATP on Ca2+ dependent exocytosisin pancreatic beta cells," *Proc. Natl. Acad. Sci. USA* 96:760-765 (1999).

Takasugi et al., "The role of presenilin cofactors in the gamma-secretase complex," *Nature* 422:438-441 (2003).

Wallberg et al., "p300 and PCAF act cooperatively to mediate transcriptional activation from chromatin templates by notch intracellular domains in vitro," *Mol. Cell Biol.* 22:7812-7819 (2002).

Wang et al., "Experimental Models of Transcription Factor-Associated Maturity-Onset Diabetes of the Young," *Diabetes* 51(3):S333-S342 (2002.

Wang et al., "GIP regulates glucose transporters, hexokinases, and glucose-induced insulin secretion in RIN 1046-38 cells," *Mol. Cell. Endocrinol.* 116:81-87 (1996).

Wang et al., "Glucagon-like Peptide-1 can reverse the age-related decline in glucose tolerance in rats," *J. Clin. Invest.* 99:2883-2889 (1997).

Wang et al., "Glucagon-like peptide-1 causes pancreatic duodenal homeobox-1 protein translocation from the cytoplasm to the nucleus of pancreatic β-cells by a cyclic adenosine monophosphate/protein kinase A-dependent mechanism," *Endocrinology* 142:1820-1827 (2001).

Withers et al., "Disruption of IRS-2 causes type 2 diabetes in mice," *Nature* 391:900-904 (1998).

Yang et al., "Requirement of Math1 for secretory cell lineage commitment in the mouse intestine," *Science* 294(5549):2155-2158 (2001).

Zhou et al., "Glucagon-like peptide-1 and exendin-4 convert pancreatic into glucagon and insulin producing cells," *Diabetes* 48:2368-2366 (1999).

International Preliminary Report on Patentability for PCT/US2005/026267.

* cited by examiner

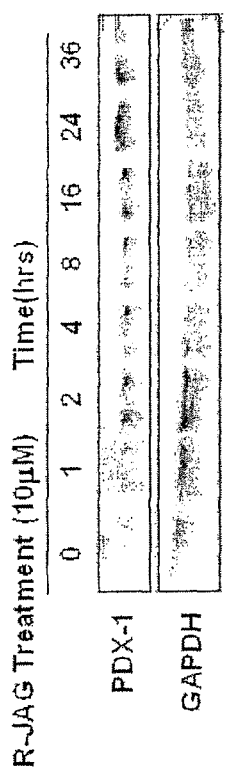
Figure 6
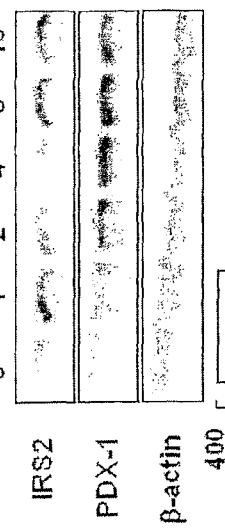
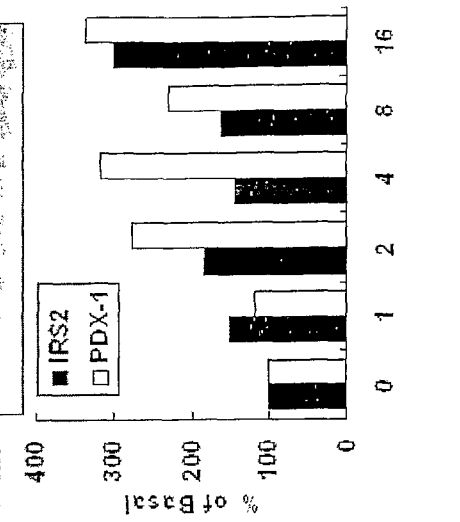
Figure 8
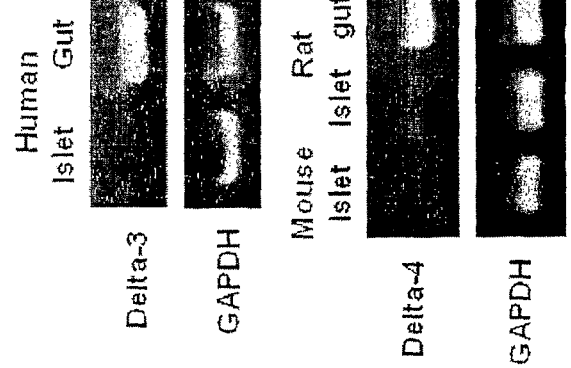
Figure 7
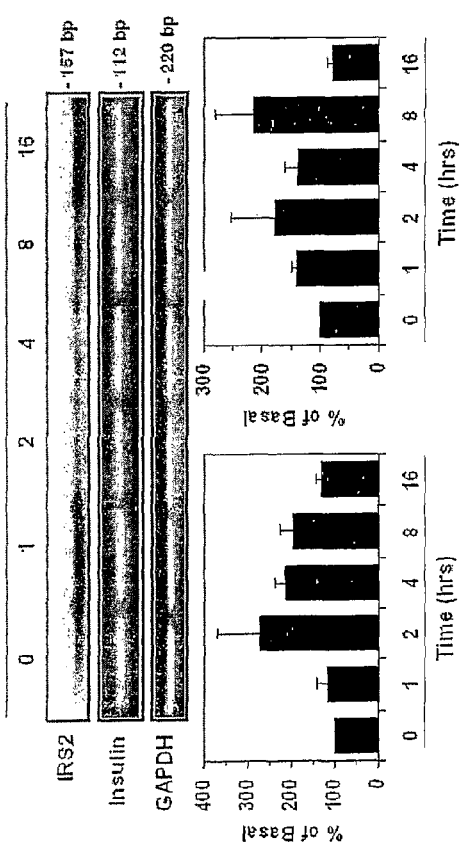

SEQUENCE LISTING

<160> NUMBER OF SEQ ID NOS: 59

<210> SEQ ID NO 1
<211> LENGTH: 19
<212> TYPE: PRT
<213> ORGANISM: Artificial Sequence
<220> FEATURE:
<223> OTHER INFORMATION: Description of artificial sequence:/note =
      synthetic construct

<400> SEQUENCE: 1

Cys Asp Asp Tyr Tyr Tyr Gly Phe Gly Cys Asn Lys Phe Gly Arg Pro
1               5                   10                  15

Arg Asp Asp

<210> SEQ ID NO 2
<211> LENGTH: 17
<212> TYPE: PRT
<213> ORGANISM: Artificial Sequence
<220> FEATURE:
<223> OTHER INFORMATION: Description of artificial sequence:/note =
      synthetic construct

<400> SEQUENCE: 2

Cys Asp Asp Tyr Tyr Tyr Gly Phe Gly Cys Asn Lys Phe Cys Arg Pro
1               5                   10                  15

Arg

<210> SEQ ID NO 3
<211> LENGTH: 17
<212> TYPE: PRT
<213> ORGANISM: Artificial Sequence
<220> FEATURE:
<223> OTHER INFORMATION: Description of artificial sequence:/note =
      synthetic construct

<400> SEQUENCE: 3

Arg Cys Gly Pro Asp Cys Phe Asp Asn Tyr Gly Arg Tyr Lys Tyr Cys
1               5                   10                  15

Phe

<210> SEQ ID NO 4
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 4
ccaaaaccgt cgcatgaagt g                                            21

<210> SEQ ID NO 5
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 5
cagctcgcct ggtggctgt                                               19

<210> SEQ ID NO 6
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 6 tacccccagcc agtgtcaaca                                              20

<210> SEQ ID NO 7
<211> LENGTH: 25
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 7
tccatgatag gctttgatga ctttc                                         25

<210> SEQ ID NO 8
<211> LENGTH: 23
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 8
tgaccagcta caatcataga cca                                           23

<210> SEQ ID NO 9
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 9
ctccagtgcc aaggtctga                                                19

<210> SEQ ID NO 10
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 10
gagccttcag tagccacagg                                               20

<210> SEQ ID NO 11
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 11
caggcgtggt tagggagtaa                                               20

<210> SEQ ID NO 12

```
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 12
cagggcattg taaccaactg                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 13
aggaaggaag gctggaagag                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 14
caggcaatcc gaggactatg                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 15
caggcgtgtt gttctcacag                                                   20

<210> SEQ ID NO 16
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 16
tgagtaggct ccatccagtc                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 17
tggtgtcagg tagggatgct                                                   20

<210> SEQ ID NO 18
<211> LENGTH: 20
```

```
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 18
tcttgctgct ggtcattctc                                           20

<210> SEQ ID NO 19
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 19
tgcctcatcc tcttcagttg                                           20

<210> SEQ ID NO 20
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 20
cactgagcca aggcatagac                                           20

<210> SEQ ID NO 21
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 21
atctccacct cacaccactg                                           20

<210> SEQ ID NO 22
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 22
tgcctgtgca caccattctg c                                         21

<210> SEQ ID NO 23
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 23
caatcagaga tgttgaggtg c                                         21

<210> SEQ ID NO 24
<211> LENGTH: 20
<212> TYPE: DNA
```

```
<213> ORGANISM: Artificial Sequence
<220> FEATURE:
<223> OTHER INFORMATION: Description of artificial sequence:/note =
      synthetic construct

<400> SEQUENCE: 24
atgcaccatg acatcgttcg                                                    20

<210> SEQ ID NO 25
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 25
gatagagtca ctgagctctc g                                                  21

<210> SEQ ID NO 26
<211> LENGTH: 22
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 26
ttggtctgct caatcctgta gc                                                 22

<210> SEQ ID NO 27
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 27
tggcattggt agcagttgct g                                                  21

<210> SEQ ID NO 28
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 28
aagcgacacg tacgagtctg g                                                  21

<210> SEQ ID NO 29
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 29
atagttgcca gctacttgtg g                                                  21

<210> SEQ ID NO 30
<211> LENGTH: 19
<212> TYPE: DNA
<213> ORGANISM: Artificial Sequence
```

```
<220> FEATURE:
<223> OTHER INFORMATION: Description of artificial sequence:/note =
      synthetic construct

<400> SEQUENCE: 30
accctgtgtg agcgaaacg                                                        19

<210> SEQ ID NO 31
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 31
catcacggca aactccaaag                                                       20

<210> SEQ ID NO 32
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 32
tcgctgtatc tgtccacctg                                                       20

<210> SEQ ID NO 33
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 33
agtcactggc acggttgtag                                                       20

<210> SEQ ID NO 34
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 34
gattggcggc tattactgtg                                                       20

<210> SEQ ID NO 35
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 35
aggcagtcgt caatgttctc                                                       20

<210> SEQ ID NO 36
<211> LENGTH: 21
<212> TYPE: DNA
<213> ORGANISM: Artificial Sequence
<220> FEATURE:
```

<223> OTHER INFORMATION: Description of artificial sequence:/note =
      synthetic construct

<400> SEQUENCE: 36
tgtgtgaagt tggaagcatc c                                            21

<210> SEQ ID NO 37
<211> LENGTH: 22
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 37
atcttgagct tggtaatagc ac                                           22

<210> SEQ ID NO 38
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 38
aaggacatac tctaccagtg c                                            21

<210> SEQ ID NO 39
<211> LENGTH: 21
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 39
acgtccttgg tacttctgac g                                            21

<210> SEQ ID NO 40
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 40
agacggagac catgaacaac                                              20

<210> SEQ ID NO 41
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 41
tcctcggata tgacgtacac                                              20

<210> SEQ ID NO 42
<211> LENGTH: 20
<212> TYPE: DNA
<213> ORGANISM: Artificial Sequence
<220> FEATURE:
<223> OTHER INFORMATION: Description of artificial sequence:/note = synthetic construct

<400> SEQUENCE: 42
gtgaatgccg atgcctagag                                               20

<210> SEQ ID NO 43
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 43
ggtccatctg cacatgtcac                                               20

<210> SEQ ID NO 44
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 44
tgaccacttc ggccactatg                                               20

<210> SEQ ID NO 45
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 45
agttggagcc ggtgaagttg                                               20

<210> SEQ ID NO 46
<211> LENGTH: 18
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 46
aagatggaag cgatgtgg                                                 18

<210> SEQ ID NO 47
<211> LENGTH: 18
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 47
tcttcaaagc aactgtcc                                                 18

<210> SEQ ID NO 48
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

```
<400> SEQUENCE: 48
ttgtggtgtc caatctctac                                                    20

<210> SEQ ID NO 49
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 49
tggatctctg tgagttcgag                                                    20

<210> SEQ ID NO 50
<211> LENGTH: 22
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 50
aacacaaacc agaagaagga gc                                                 22

<210> SEQ ID NO 51
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 51
ggcgaccaca aacaggaag                                                     19

<210> SEQ ID NO 52
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 52
tgtggttctc acttggtgga                                                    20

<210> SEQ ID NO 53
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 53
gctccagttg tgccacttgt                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of artificial sequence:/note =
      synthetic construct
```

```
<400> SEQUENCE: 54
cctaagcaga tcctgcaacc                                               20

<210> SEQ ID NO 55
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 55
attcgcatgt acccgctatc                                               20

<210> SEQ ID NO 56
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 56
gaaggtgaag gtcggagtc                                                19

<210> SEQ ID NO 57
<211> LENGTH: 20
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 57
gaagatggtg atgggatttc                                               20

<210> SEQ ID NO 58
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 58
tgcaccacca actgcttag                                                19

<210> SEQ ID NO 59
<211> LENGTH: 19
<212> TYPE: DNA
<213> ORGANISM: Artificial Sequence
<220> FEATURE:
<223> OTHER INFORMATION: Description of artificial sequence:/note =
      synthetic construct

<400> SEQUENCE: 59
ggatgcaggg atgatgttc                                                19
```

USES OF NOTCH RECEPTORS, NOTCH LIGANDS, AND NOTCH MODULATORS IN METHODS RELATED TO METABOLIC DISEASES

BACKGROUND

Notch Signaling

Notch signaling is a mechanism conserved through evolution and plays a role in determining cell fate choices during the development of many cell lineages in both vertebrates and invertebrates. The cellular responses to Notch signaling activation that have been characterized so far are, for example, differentiation, proliferation, and/or apoptosis, depending on the specific point in the cell cycle and the specific cell type. In addition to its role as a signal-transducing cell surface protein, Notch can also directly regulate gene transcription.

Four mammalian Notch receptors (Notch-1, Notch-2, Notch-3, and Notch-4) and five Notch ligands (delta-like ligands-1, -3, and -4 and Jagged-1 and -2) have been identified (Artavanis-Tsakonas, et al., *Science*, 284:770-776 (1999)). The Notch receptors are typically large (generally about 300 kDa) single pass transmembrane receptors initially identified in the fruit fly (the phenotype of the Notch-1 mutant allele has notched wings). The Notch receptors have an extracellular domain with numerous (usually over 30) EGF-like repeats, three membrane-proximal Notch-specific repeats, and an intracellular domain that contains four functional regions. These four intracellular functional regions are the RAM domain, the 6 ankyrin repeats, a transcriptional factor activation domain (TAD), and the proline, glutamate, serine, and threonine-rich PEST sequence. Also, there are two nuclear localization sequences both before and after the ankyrin repeats.

Typically, Notch receptors are synthesized in the endoplasmic reticulum and are then cleaved in an established three step proteolytic model of Notch activation. The initial cleavage results from activation of a furin-like convertase in the trans-Golgi network and occurs at site 1, between the Notch EGF repeats and the transmembrane domain. The resulting halves re-associate via a calcium-dependant, non-covalent bond (Rand, et al., *Mol Cell Biol*, 20:1825-1835 (2000)). This heterodimer migrates to the cell surface where cell-membrane-associated ligands on the adjacent cell bind to and activate the Notch receptors. Activation of the Notch receptor by these ligands triggers the second cleavage of the extracellular portion of the Notch receptor by the metalloprotease TACE (TNF-α-converting enzyme). This is followed by the cleavage of Notch from the membrane by the presenilin-dependent γ-secretase complex, which releases the cytosolic fragment known as the Notch intracellular domain (NICD) (Fortini, *Nature Rev*, 3:673-684 (2002)).

NICD is approximately 80 kDa in length and binds to a number of transcription factors, including RBP-Jκ, which together with NICD forms a complex that promotes transcription of the Hairy Enhancer of Split (HES) (Jarriault, et al., *Mol Cell Biol*, 18:7423-7431 (1998)), HERP, and HEY gene families. HES acts a transcriptional factor repressor of, amongst others, genes associated with stem cells of the gut such as ngn3 (Lee, et al., *Diabetes*, 50(5):928-936 (2001)) and Math1 (Yang, et al., *Science*, 294(5549):2155-2158 (2001)). Thus, to date the Notch signaling pathway is known to comprise the Notch ligands delta-like ligands-1, -3, and -4 and Jagged-1 and -2; the Notch receptors Notch-1 through Notch-4; intracellular effectors CBF-1, Deltex, and NF-κB; the Notch target genes HES, HERP, HEY, and bHLH; processing molecules Kuzbanian, TACE, sel1L, and presenilin; and factors known to regulate Notch pathway activity such as numb, numb-like, and disheveled-1, -2, and -3, as well as fringe family members lunatic fringe, manic fringe, and radical fringe.

Diabetes and the Pancreas

Blood glucose levels are controlled by the release of insulin from the β-cells of the islets of Langerhans in the endocrine portion of the pancreas. Diabetes is basically a lack of sufficient functional β-cell mass to control increases in blood glucose. There are two main categories of diabetes: type 1 (commonly referred to as childhood diabetes) in which there are no β-cells and type 2 (or late onset diabetes) in which insulin secretion is altered and results from a failure of the β-cells to produce sufficient insulin to meet the demands of the body.

Currently, nearly 18.2 million people (6.3% of the population) in the US have diabetes. Of those, 13 million carry the diagnoses but nearly a third (5.2 million) have not been diagnosed. Of those Americans that have been diagnosed with diabetes, approximately 5-10% suffer from type-1 diabetes and 90-95% suffer from type-2 diabetes. Diabetes presently costs $132 billion in health care expenditure in the US alone (Diabetes Care, Economic Costs of Diabetes in the U.S. 2002-2003, 26: 917-932).

Type-1 diabetes results primarily from an autoimmune destruction of the β-cells that secrete insulin. Thus, there is usually a complete deficiency of insulin in this state and patients are required to take insulin injections to survive. Patients suffering from type-2 diabetes have abnormal insulin secretion and therefore may not be dependent on insulin unless control of blood glucose is not achieved by diet and exercise and oral hypoglycemic agents. Medications currently in use to treat type-2 diabetes have limited success in controlling blood glucose levels, hence, the complications of the disease (United Kingdom Prospective Diabetes Study, 1998). An ongoing failure in β-cell function is another aspect of this disease that none of the currently used medications is capable of reversing (United Kingdom Prospective Diabetes Study, 1995).

There is a third form of diabetes referred to as maturity onset diabetes of the young or MODY. So called as its onset has many of the classical symptoms associated with type-2 diabetes but occurs in the younger population range where the average age at which symptoms present is usually before 25 years of age (Fajans, et al., *N Eng J Med*, 13:971-980 (2001)). The symptoms of MODY are associated with disrupted expression of genes for proteins that are essential for the maintenance of β-cell function and mass. There are currently 6 defined MODY types, MODY-1, -2, -3, -4, -5, and -6, connected with HNF-4α, glucokinase, HNF-1α, PDX-1, HNF-1β, and, β2/NeuroD genes, respectively.

Insulin is secreted in exquisitely controlled amounts in response to increases in blood glucose. Current medications that affect, β-cells and insulin secretion directly are the class of drugs which act as potassium channel closers; these drugs are divided into two groups, the sulfonylureas and the benzoic acid derivatives (also referred to as meglitinides). These drugs act to depolarize the membrane potential of the β-cell by closing the $K_{ATP}$ channels, thereby increasing the release of insulin secretory granules from the ready releasable pool. They do not increase insulin synthesis nor do they improve the responsiveness of the β-cell to rising blood glucose levels. Glucagon-like-peptide-1 (GLP-1) receptor analogs have been shown to increase insulin secretion, insulin synthesis and to sensitize the response of the β-cells to changes in blood glucose. (Drucker D. J. Glucagon-like peptide-1 and the islet, β-cell; augmentation of cell proliferation and inhibition of apoptosis. *Endocrinology* 144:5145-5148, (2003)). They improve insulin secretion by acting at several points of the insulin secretion pathway. GLP-1 receptor activation is currently the only pharmacological agent that increases insulin transcription and translation, i.e., enhances insulin synthesis and secretion in the β-cell. It is also the only compound which apparently improves long term function of the β-cell as indicated by a restoration of first phase insulin secretion in patients with type-2 diabetes.

In light of the prevalence and seriousness of diabetes, as well as other metabolic disorders, there exists a need for new diagnostic, therapeutic, and preventative processes and compositions. The disclosed subject matter addresses this need.

SUMMARY

In accordance with the purposes of the disclosed materials, compositions, and methods, as embodied and broadly described herein, the disclosed subject matter, in one aspect, relates to methods for identifying and isolating a pancreatic precursor cell. Also, the disclosed subject matter relates to methods of increasing insulin synthesis from a pancreatic β-cell. Further, the disclosed subject matter relates to methods of improving pancreatic β-cell function. Still further, the disclosed subject matter relates to methods of preventing or delaying the onset of a metabolic disease, methods of treating or preventing a metabolic disease in a subject, and to compositions for treating or preventing a metabolic disease in a subject in need of such treatment or prevention. The disclosed subject matter also relates to methods for stimulating or promoting the differentiation of pancreatic precursor cells.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying Figures, which are incorporated in and constitute a part of this specification, illustrate several aspects described below.

FIG. 1A demonstrates RT-PCR analysis of expression of Notch, Jagged and Delta in isolated islets and clonal rat β-cells (RIN 1046-38 cells). FIG. 1B demonstrates immunohistochemistry showing Notch-1 in islets of fixed rat (fasted) and human (metabolic state unknown) pancreata. Arrowheads show nuclear Notch. FIG. 1C demonstrates immunohistochemistry showing Jagged-1 in a human islet and ducts (arrow) and indirect immunofluorescence for Jagged-1 in RIN cells. Scale bar represents 75 μm.

FIG. 2A demonstrates immunofluorescence of NICD in response to glucose and R-JAG. FIG. 2B demonstrates an immunoblot of nuclear extracts from cells stimulated with glucose and two Jagged-related peptides, showing the 80 kDa NICD fragment. FIG. 2C demonstrates an immunoblot of nuclear extracts showing the additive effect of glucose and R-JAG on nuclear NICD. Notch-1 protein levels were normalized to TFIIH, results are mean±SE, n=9 (glucose) and n=3 (Jagged-related peptides).

FIG. 3A demonstrates increase in rat insulin 1 promoter activity, t $p<0.001$ compared to no treatment, †† $p<0.001$ compared to glucose only treatment, \\\\ $p<0.001$ compared to Ex-4 or R-JAG single treatment. FIG. 3B demonstrates intracellular insulin in cells following 6 h treatment, \ $p<0.05$ compared to no treatment, \\\\ $p<0.05$ compared to glucose only treatment. FIG. 3C demonstrates time course of insulin release into the medium. Glu (glucose), t $p<0.05$ compared to no or glucose only treatment, \\\\ $p<0.01$ compared to no or glucose only treatment. FIG. 3D demonstrates total insulin released into the medium following 6 h treatment, \ $p<0.05$ compared to Ex-4 or R-JAG treatment, \\\\ $p<0.001$ compared to Ex-4 or R-JAG treatment. *Replenishing R-JAG 2 hourly, results are mean±SE, n=3-5.

FIG. 4A demonstrates [$^3$H] thymidine uptake in RIN cells following 8 h treatment. *Replenishing R-JAG 2 hourly, \ $p<0.05$ compared to 2 or 6.3 mM glucose treatment, results are mean±SE, n=4. FIG. 4B demonstrates immunoblotting of whole RIN cell extracts previously treated with R-JAG (10 μM) for IRS2 and Notch-1 normalized to β-actin, one representative experiment, n=3. FIG. 4C demonstrates immunoblotting for IRS2 and PDX-1, normalized to Erk, of whole cell extracts from C57/BL6 mouse islets treated for 8 h, *replenishing R-JAG 2 hourly, results are mean±SE, n=3 islet isolates, 4 pancreata per isolate.

FIG. 5A demonstrates indirect immunofluorescence of cells treated with secretagogues, and PKA and γ-secretase inhibitors, as indicated. FIG. 5B demonstrates immunoblotting of nuclear extracts from cells treated with secretagogues and PKA and γ-secretase inhibitors as indicated. One representative experiment, n=3. Notch-1 protein levels normalized to TFIIH levels. FIG. 5C demonstrates Ex-4 activated γ-secretase cleavage of the N-terminus of membrane tethered NICD is abrogated by L-685,458 and H89. Results are mean±SE, n=3.

FIG. 6 shows that RT-PCR demonstrates the expression of Delta-3 and -4 in rodent and human gut (Histology Control Systems), but lack of expression of Delta-3 in human islets and lack of Delta-4 in rodent islets.

FIG. 7 shows the RT-PCR (27 cycles) time course for rat IRS2 and insulin mRNA in RIN cells after single R-JAG treatment, relative amounts normalized to GAPDH. The effects of R-JAG diminished after 8 h. Replenishing R-JAG every 2 h resulted in sustained elevations.

FIG. 8 shows an immunoblot of whole cell extract from RIN cells for PDX-1 in R-JAG treated RIN cells and for IRS2 and PDX-1 in Exendin-4 treated RIN cells (relative amounts normalized to β-actin).

DETAILED DESCRIPTION

Figure 1:
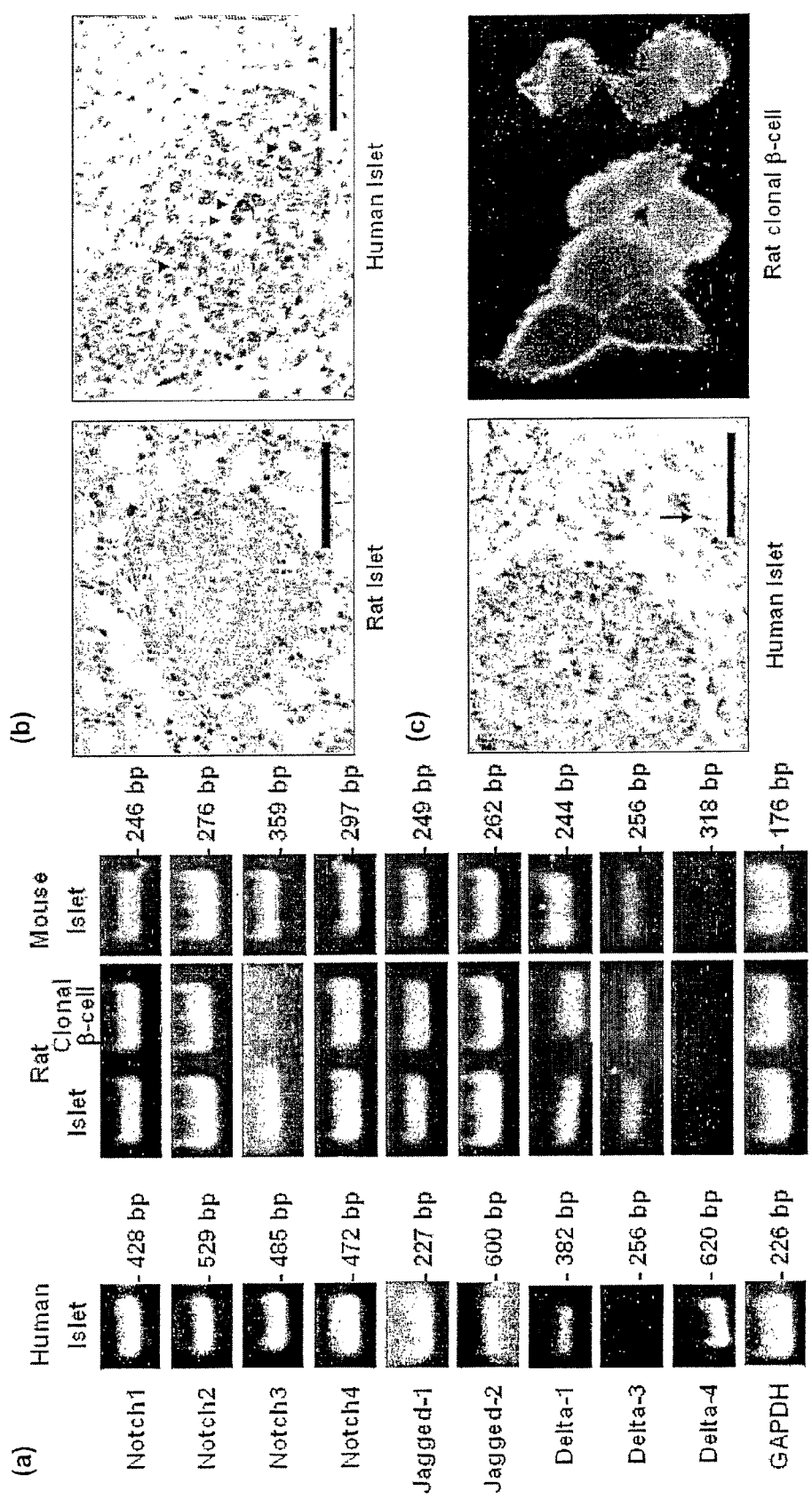
FIGS. 1A-C show that both rodent and human adult islets express Notch receptors and their ligands.

The materials, compositions, and methods described herein may be understood more readily by reference to the following detailed description of specific aspects of the disclosed subject matter, the methods and the Examples included therein, and to the Figures and their previous and following description.

Before the present materials, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Disclosed herein are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide or nucleic acid is disclosed and a number of modifications that can be made to a number of amino acid residues or nucleotides, including those related to the Notch receptor and Notch receptor ligands, are discussed, each and every combination and permutation that are possible are specifically contemplated unless specifically indicated to the contrary. Thus, if a class of substituents A, B, and C are disclosed as well as a class of substituents D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Throughout this specification, various publications are referenced. The disclosures of these publications are hereby incorporated by reference into this disclosure in order to more fully describe the state of the art to which this disclosure pertains. The referenced publications disclosed are incorporated by reference herein for the material contained in them that is discussed in the sentence and/or preceding sentence in which the reference is relied upon. Also, it is to be understood that the fact this disclosure contains specific incorporations by reference for some referenced publications and not others is not meant to imply that other publications without such specific incorporations by reference are not also intended to be incorporated as stated above.

DEFINITIONS

In this specification and in the claims that follow, reference will be made to a number of terms, which shall be defined to have the following meanings:

As used in the specification and the appended claims, the singular forms "a," "an," and "the" include plural referents unless the context clearly dictates otherwise. Thus, for example, reference to "a nucleotide" includes mixtures of two or more such nucleotides, reference to "an amino acid" includes mixtures of two or more such amino acids, reference to "the Notch receptor" includes mixtures of two or more such Notch receptors, and the like.

"Optional" or "optionally" means that the subsequently described event or circumstance can or cannot occur, and that the description includes instances where the event or circumstance occurs and instances where it does not.

Ranges can be expressed herein as from "about" one particular value and/or to "about" another particular value. When such a range is expressed, another aspect includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that the throughout the application data are provided in a number of different formats and that this data represents endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15.

"Subject," as used herein, means an individual. In one aspect, the subject is a mammal such as a primate, and, in another aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

The terms "higher," "increases," "elevates," or "raises" refer to increases above control levels, e.g., as compared to a basal level or as compared to an untreated control level. The terms "lower," "decreases," "reduces," or "reduction" refer to decreases below control levels, e.g., as compared to a basal levels or as compared to an untreated control level. By "control" is meant either a subject lacking a disease or a subject in the absence of a particular variable such as a therapeutic. A subject in the absence of a therapeutic can be the same subject before or after treatment with a therapeutic or can be a different subject in the absence of the therapeutic. Comparison to a control can include a comparison to a known control level or value known in the art. Thus, basal levels are normal in vivo levels prior to, or in the absence of, addition of an agent or another small molecule or ligand.

"Deletion," as used herein, refers to a change in an amino acid or nucleotide sequence in which one or more amino acid or nucleotide residues, respectively, are absent relative to the reference sequence.

"Insertion" or "addition," as used herein, refers to a change in an amino acid or nucleotide sequence resulting in the addition of one or more amino acid or nucleotide residues, respectively, as compared to the reference sequence.

"Substitution," as used herein, refers to the replacement of one or more amino acids or nucleotides by one or more different amino acids or nucleotides, respectively, in a reference sequence.

"Isolated," as used herein, refers to material, such as a nucleic acid or a polypeptide, which is: (1) substantially or essentially free from components that normally accompany or interact with it as found in its naturally occurring environment. Although, the isolated material optionally comprises material not found with the isolated material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state.

There are a variety of compositions disclosed herein that are amino acid based, including, for example, Notch receptors and Notch receptor ligands. Thus, as used herein, "amino acid" and "amino acid residue" means the typically encountered twenty amino acids which make up polypeptides; e.g., alanine (i.e., A or Ala), cysteine (i.e., C or Cys), aspartic acid (i.e., D or Asp), glutamic acid (i.e., E or Glu), phenylalanine (i.e., F or Phe), glycine (i.e., G or Gly), histidine (i.e., H or His), isoleucine (i.e., I or Ile), lysine (i.e., K or Lys), leucine (i.e., L or Leu), methionine (i.e., M or Met), asparagine (i.e., N or Apn), proline (i.e., P or Pro), glutamine (i.e., Q or Gln), arginine (i.e., R or Arg), serine (i.e., S or Ser), threonine (i.e., T or Thr), valine (i.e., V or Val), tryptophan (i.e., W or Trp), and tyrosine (i.e., Y or Tyr). In addition, it further includes less typical constituents which are both naturally occurring, such as, but not limited to, formylmethionine and selenocysteine, analogs of typically found amino acids, and mimetics of amino acids or amino acid functionalities. Non-limiting examples of these and other molecules are discussed herein.

As used herein, the terms "peptide" and "polypeptide" refer to a class of compounds composed of amino acids chemically bonded together. Non-limiting examples of these and other molecules are discussed herein. In general, the amino acids are chemically bonded together via amide linkages (CONH); however, the amino acids can be bonded together by other chemical bonds known in the art and described further herein (e.g., peptide derivatives, analogs, and variants). For example, the amino acids can be bonded by amine linkages. Also, "peptide" as used herein includes oligomers of amino acids and small and large peptides, including polypeptides and proteins.

As disclosed herein there are numerous variants of proteins (e.g., Notch receptors and Notch receptor ligands) that are contemplated herein. In addition, to the known functional Notch receptor ligand and receptor strain variants there are derivatives of these proteins which also function in the disclosed methods and compositions. Protein variants and derivatives are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than from about 2 to about 6 residues are deleted at any one site within the protein molecule. These variants can ordinarily be prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single amino acid residues, but can occur at a number of different locations at once; insertions usually can be on the order of from about 1 to about 10 amino acid residues; and deletions can range from about 1 to about 30 residues. Deletions or insertions can be made in adjacent pairs, i.e., a deletion of 2 amino acid residues or insertion of 2 amino acid residues. Substitutions, deletions, insertions or any combination thereof may be combined to arrive at a final construct. Substitutional variants are those in which at least one amino acid residue has been removed and a different residue inserted in its place. Such substitutions generally are made in accordance with the following Table 1 and are referred to as conservative substitutions.

TABLE 1

Amino Acid Substitutions
Original Residue Exemplary Conservative
Substitutions, others are known in the art.

Ala ↔ Ser
Arg ↔ Lys; Gln
Asn ↔ Gln; His
Asp ↔ Glu
Cys ↔ Ser

TABLE 1-continued

Amino Acid Substitutions
Original Residue Exemplary Conservative
Substitutions, others are known in the art.

| | |
|---|---|
| Gln | ↔ Asn or Lys |
| Glu | ↔ Asp |
| Gly | ↔ Pro |
| His | ↔ Asn or Gln |
| Ile | ↔ Leu or Val |
| Leu | ↔ Ile or Val |
| Lys | ↔ Arg or Gln |
| Met | ↔ Leu or Ile |
| Phe | ↔ Met, Leu, or Tyr |
| Ser | ↔ Thr |
| Thr | ↔ Ser |
| Trp | ↔ Tyr |
| Tyr | ↔ Trp or Phe |
| Val | ↔ Ile or Leu |

Substantial changes in function can be made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another or one polar residue for another. The substitutions include combinations such as Gly, Ala; Val, Ile, Leu; Asp, Glu; Asn, Gln; Ser, Thr; Lys, Arg; and Phe, Tyr. Such conservatively substituted variations of each explicitly disclosed sequence are included within the polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g., Arg, can be accomplished, for example, by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the O-amino groups of lysine, arginine, and histidine side chains (Creighton, Proteins: Structure and Molecular Properties, W.H. Freeman & Co., San Francisco pp. 79-86 (1983), which is incorporated by reference herein for its material on post-translational derivatizations), acetylation of the N-terminal amine and, in some instances, amidation of the C-terminal carboxyl.

It is understood that one way to define the variants, derivatives, and analogs of the peptides and proteins disclosed herein is through defining the variants, derivatives, and analogs in terms of homology/identity to specific known sequences. For example, SEQ ID NO:1 sets forth a particular sequence of Jagged peptide R-JAG and SEQ ID NO:2 sets forth a particular sequence of a Jagged peptide JAG-1. Specifically disclosed are variants, derivatives, and analogs of these and other peptides and proteins herein disclosed which have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman, *Adv Appl Math,* 2:482 (1981), by the homology alignment algorithm of Needleman and Wunsch, *J Mol Biol,* 48:443 (1970), by the search for similarity method of Pearson and Lipman, *Proc Natl Acad Sci,* 85:2444 (1988), by computerized implementations of these algorithms (GAP, BESTFIT, FASTA, and TFASTA in the Wisconsin Genetics Software Package, Genetics Computer Group (Madison, Wis.), all of which are incorporated by reference herein for their methods and algorithms for determining homology). Homology can also be determined by inspection.

It is understood that the description of conservative mutations and homology can be combined together in any combination, such as peptides that have at least 70% homology to a particular sequence wherein the variants are conservative mutations.

As used herein, a sequence recited as having a particular percent homology to another sequence refers to sequences that have the recited homology as calculated by any one or more of the calculation methods described above. For example, a first sequence has 80% homology, as defined herein, to a second sequence if the first sequence is calculated to have 80% homology to the second sequence using the Smith and Waterman calculation method even if the first sequence does not have 80% homology to the second sequence as calculated by any of the other calculation methods. As another example, a first sequence has 80% homology, as defined herein, to a second sequence if the first sequence is calculated to have 80% homology to the second sequence using both the Smith and Waterman calculation method and the Pearson and Lipman calculation method even if the first sequence does not have 80% homology to the second sequence as calculated by the Needleman and Wunsch calculation method, or any of the other calculation methods. As yet another example, a first sequence has 80 percent homology, as defined herein, to a second sequence if the first sequence is calculated to have 80% homology to the second sequence using each of calculation methods (although, in practice, the different calculation methods will often result in different calculated homology percentages).

It is further understood that there are numerous amino acid and peptide analogs that can be incorporated into the disclosed compositions. For example, there are numerous D amino acids or amino acids which have a different functional substituent then the amino acids described above. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson, et al., *Methods in Molec Biol,* 77:43-73 (1991), Zoller, *Curr Opin Biotech,* 3:348-354 (1992); Ibba, *Biotech & Gen Eng Rev,* 13:197-216 (1995), Cahill, et al., *TIBS,* 14(10):400-403 (1989); Benner, *TIB Tech,* 12:158-163 (1994); Ibba and Hennecke, *Bio/technology,* 12:678-682 (1994), all of which are incorporated by reference herein for their material related to amino acid analogs).

It is further contemplated that molecules can be produced that resemble peptides disclosed herein, but which are not connected via a natural peptide linkages. For example, peptide analogs can have linkages for amino acids or amino acid analogs that include —$CH_2NH$—, —$CH_2S$—, —$CH_2$—$CH_2$—, —CH=CH— (cis and trans), —$COCH_2$—, —CH(OH)$CH_2$—, and —$CH_2SO$— (These and others can be found in Spatola, in Chemistry and Biochemistry of Amino Acids, Peptides, and Proteins, B. Weinstein, eds., Marcel Dekker, New York, p. 267 (1983); Spatola, Vega Data (March 1983), Vol. 1, Issue 3, Peptide Backbone Modifications (general review); Morley, *Trends Pharm Sci* (1980) pp. 463-468; Hudson, et al., *Int J Pept Prot Res,* 14:177-185 (1979) (—$CH_2NH$—, —$CH_2CH_2$—); Spatola, et al., *Life Sci,* 38:1243-1249 (1986) (—$CH_2S$—); Hann, *J Chem Soc, Perkin Trans I,* 307-314 (1982) (—CH=CH—, cis and trans); Almquist, et al., *J Med Chem,* 23:1392-1398 (1980) (—$COCH_2$—); Jennings-White, et al., *Tetrahedron Lett,* 23:2533 (1982) (—$COCH_2$—); Szelke, et al., *European Appln,* EP 45665 CA (1982): 97:39405 (1982) (—CH(OH)$CH_2$—); Holladay, et al., *Tetrahedron Lett,* 24:4401-4404 (1983) (—CH(OH)$CH_2$—); and Hruby, *Life Sci,* 31:189-199 (1982) (—$CH_2S$—); each of which is incorporated by reference herein for its material regarding peptide analogs, mimetics, and non-peptide linkages). Also, it is understood that peptide analogs can have more than one atom between the bond atoms, such as β-alanine, γ-aminobutyric acid, and the like.

Amino acid analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others. For example, D-amino acids and β-amino acids can be used to generate more stable peptides, because these amino acids are not recognized by peptidases and such. Systematic substitution of one or more amino acids of a consensus sequence with a D- or β-amino acid of the same type (e.g., D-lysine in place of L-lysine or β-alanine in place of alanine) can be used to generate more stable peptides. Cysteine residues can be used to cyclize or attach two or more peptides together. This can be beneficial to constrain peptides into particular conformations (Rizo and Gierasch, *Ann Rev Biochem,* 61:387 (1992)).

Reference will now be made in detail to specific aspects of the disclosed materials, compounds, compositions, articles, and methods, examples of which are illustrated in the accompanying Examples and Figures.

Compositions and Methods

Diabetes (e.g., Type-2 diabetes) is associated with the deficiency of insulin. In some patients, this deficiency may be a result of non-functional β-cell mass that may fail to produce sufficient quantities of insulin to maintain euglycemia. Disclosed herein are compositions and methods that, in many examples, pertain to the use of Notch receptors, ligands, and downstream signaling molecules for improving the function of the insulin secreting cell and for inducing insulin synthesis by inducing insulin transcription and key β-cell genes including, but not limited to, IRS-2 and PDX-1. Also disclosed herein are methods and compositions that, in certain examples, use Notch signaling to cause differentiation of pancreatic islet precursor cells into insulin secreting cells. The four known Notch receptors and the five ligands are expressed in the adult pancreas and (with the exception of delta 3 in the human and delta 4 in the rat) are components of the insulin secreting, islet β-cells. Activation of the Notch pathway using soluble Notch ligands is demonstrated herein to increase insulin gene transcription and subsequent insulin release. This treatment also up-regulates the key β-cell genes PDX-1 and IRS-2, which are essential to β-cell function and survival. Also glucagon-like peptide-1 (GLP-1) receptor agonists activate Notch by activating γ-secretase.

Methods for Identifying and Isolating a Precursor Cell

In one aspect, disclosed herein are methods for identifying a precursor cell, such as a pancreatic precursor cell, comprising contacting a cell sample, such as a pancreatic cell sample, with a marker that selectively binds a Notch receptor and detecting the bound marker, the cell that binds the marker being a precursor cell. In a further aspect, disclosed herein are methods for isolating a precursor cell, such as a pancreatic precursor cell, from a cell sample, comprising identifying a cell that comprises a Notch receptor and separating the identified cell from the cell sample, the separated cell being a precursor cell.

Precursor Cells

Various precursor cells (i.e., progenitor cells) are suitable for use in the methods disclosed herein. A precursor cell is an unspecialized cell capable of undergoing cell division or a cell that has partial characteristics of a specialized cell and is capable of undergoing cell division to yield at least two specialized cells (the two specialized cells can be the same or different types of specialized cells). The precursor cell can be totipotent, pluripotent, multipotent, or oligopotent. To be identified or isolated by the methods disclosed herein, the precursor cell expresses one or more Notch receptors. For example, the precursor cell can express one or more Notch receptors chosen from Notch-1 receptor, Notch-2 receptor, Notch-3 receptor, and Notch-4 receptor or can express any Notch ligand. That is, the precursor cell can express one or more Notch receptors comprising Notch-1 receptor, Notch-2 receptor, Notch-3 receptor, or Notch-4 receptor, including any combinations thereof, or any Notch ligand.

In one example, one or more pancreatic precursor cell can be identified and isolated by the disclosed methods. These precursor cells can be the same or different; that is, the disclosed methods can be used to identify and isolate one or more kinds of precursor cells from a cell sample and distinguish between various kinds of precursor cells in the sample. For example, the disclosed methods can be used to distinguish a pancreatic precursor cell from another kind of cell or precursor cells.

A precursor cell identified or isolated by the methods disclosed herein can be from, for example, eukaryotic species, including, but not limited to, mammals (e.g., rat, mouse, bovine, porcine, sheep, goat, and human).

Specific examples of pancreatic tissues from which a precursor cell can be identified and isolated include, but are not limited to, whole pancreas, ductal epithelium, islet, extra-islet, and the like. These precursor cells can be identified and isolated from organisms under normal basal conditions, under naturally occurring or induced disease states (e.g., diabetes), or following some sort of activation, stimulation or other perturbation of the organism, including, for example, genetic, pharmacologic, surgical, pathogenic, or therapeutic manipulations.

A precursor cell can be identified and isolated by the disclosed methods from a cell sample, e.g., a sample of cells obtained from a tissue, an organ (e.g., pancreatic cell sample), or a cell culture. The cell sample can contain the same type of cells or a mixture of different types of cells. The cells in the cell sample can be from any organism, from any tissue, and of any cell type. For example, one or more cells can be from any eukaryotic species and can be differentiated, undifferentiated, de-differentiated, or immortalized. A cell sample can contain cells of eukaryotic origin, including, but not limited to, mammalian cells (e.g., as rat, mouse, bovine, porcine, sheep, goat, dog, and human). These cells can be taken from organisms under normal basal conditions, under naturally occurring or induced disease states (e.g., diabetes), or following some sort of activation, stimulation or other perturbation of the organism, including, for example, genetic, pharmacologic, surgical, pathogenic, or therapeutic manipulations.

In one example, a pancreatic cell sample can comprise one or more cells chosen from, ductal epithelium, islet cells, and extra-islet cells. For example, a pancreatic cell sample can comprise ductal epithelium, islet cells, or extra-islet cells, including any combination thereof. Some specific examples of the various cell types that can be in the cell sample include, but are not limited to, pancreatic islet cells. In one example, the cell sample comprises a pancreatic cell sample from a subject (e.g., a human). In another example, the cell sample comprises a pancreatic cell sample from a subject with diabetes. In yet another example, the cell sample comprises an adult endocrine cell.

The choice of precursor cell and the cell sample from which the precursor cell is to be identified and/or isolated can be made by one of ordinary skill in the art. The choice will depend on the particular desires and aims of the researcher or clinician. For example, one interested in pancreatic function could decide to obtain a pancreatic precursor cell from a pancreas, i.e., a pancreatic cell sample.

Marker

A sample (e.g., a cell sample or histological sample) can be contacted with a marker that selectively binds one or more Notch receptors on a precursor cell. Specific Notch receptors that can be selectively bound by the marker include Notch-1 receptor, Notch-2 receptor, Notch-3 receptor, and Notch-4 receptor. Notch ligands can also be bound by the marker, including such ligands as Jagged-1, Jagged-2, Dll1, Dll3 and Dll4. The nucleic acid and amino acid sequences for Notch receptors 1-4 can be found at GenBank Accession Nos. NM_017617, NM_024408, NM_000435, and NM_004557, respectively and at Unigene No. Hs.311559, Hs.8121, Hs.8546, and Hs. 436100, respectively. All of the information, including any nucleic acid and amino acids sequences, fragments or variants thereof provided for the Notch receptors under these GenBank Accession Nos. and the Unigene Nos. are hereby incorporated in their entirety by this reference.

The cell sample can be contacted with a marker by submerging or immersing the cell sample in a solution containing the marker. In another example, the cell sample can be coated or sprayed with a solution containing the marker. In still another example, the cell sample can be contacted with a medium, such as a growth medium, that contains the marker. The various methods of contacting the cell sample with the markers disclosed herein will be readily apparent to one of ordinary skill in the art, depending on such factors as the type of cell, tissue, organ, or subject, the particular marker to be used, convenience, and the like. In one example, a pancreatic cell sample is contacted with a marker that selectively binds a Notch receptor. The precursor cell can express a specific sub-set of the Notch receptors and ligands that delineate from the other mature pancreatic cell types that do not have the capacity to be differentiated into multiple pancreatic cell types. The selected precursor cells could be isolated under sterile conditions, for example, in the FACS analysis based on binding of the marker to cell surface molecules like Notch ligands and receptors. Once isolated in this manner it can be cultivated and then treated to differentiate it into the desired pancreatic cell type.

"Selectively binds" or "specifically interacts" as used herein means that the marker binds only one Notch receptor and shows little or no binding to other types of receptors using traditional Western blot analysis. A marker suitable for the disclosed methods binds a Notch receptor selectively and shows no binding above about 1.5 times background for other cell surface receptors, such as, GLP-1/Ex-4 receptor, or Kir6.2.

A marker is a molecule or composition that specifically interacts with a particular molecule or moiety. In the context of the disclosed methods, the molecule or moiety that specifically interacts with a marker is generally a cell surface protein, e.g., a Notch receptor or a portion thereof. Antibodies, either member of a receptor/ligand pair, synthetic polyamides (including variants, derivatives, and analogs thereof) and other molecules with specific binding affinities are examples of markers that can be used herein. Markers are generally used to identify and isolate precursor cells and/or to target precursor cells as described herein.

A marker that specifically interacts with a particular analyte, e.g., a Notch receptor on a pancreatic precursor cell, is said to be specific for that analyte. For example, where the marker is an antibody that associates with a particular antigen, the marker is said to be specific for that antigen. The antigen is the analyte. The marker can further comprise a detectable moiety as described elsewhere herein. In one example, markers comprise antibodies, ligands, binding proteins, receptor proteins, haptens, aptamers, carbohydrates, synthetic polyamides, peptides, nucleic acids, oligonucleotides or fragments, derivatives, variants or analogs thereof.

Antibody Markers

A marker can be an antibody, such as an antibody to a Notch receptor or an epitope thereof. Antibodies useful as markers in the disclosed methods are generally specific for cell surface proteins. Numerous antibodies specific for various cell surface proteins are known, and many are commercially available. Such antibodies can be used in the disclosed methods and/or to produce components used in the disclosed methods (such as for use as markers). Useful antibodies can also be produced for use in the disclosed method. Techniques for antibody production are known, some of which are described below. Such techniques can be used to produce antibodies for use in the disclosed methods.

The terms "antibody" or "antibodies" is used herein in a broad sense and includes polyclonal, monoclonal, fully human, and humanized antibodies. In addition to intact immunoglobulin molecules, also included in the term "antibodies" are fragments or polymers of those immunoglobulin molecules, multimers of immunoglobulin molecules (e.g., diabodies, triabodies, and bi-specific, and tri-specific antibodies, as are known in the art; see, e.g., Hudson and Kortt, *J Immunol Methods*, 231:177-189 (1999)), fusion proteins containing an antibody or antibody fragment, which are produced using standard molecular biology techniques, single chain antibodies, and human or humanized versions of immunoglobulin molecules or fragments thereof, as long as they are chosen for their ability to interact with cell surface proteins (or other antibody target), as described herein.

The skilled artisan will understand that either full-length antigens or fragments thereof can be used to generate the antibodies of the disclosed methods. A polypeptide to be used for generating an antibody suitable for use in the disclosed methods can be partially or fully purified from a natural source, or can be produced using recombinant DNA techniques. For example, for antigens that are peptides or polypeptides, a cDNA encoding an antigen, or a fragment thereof, can be expressed in prokaryotic cells (e.g., bacteria) or eukaryotic cells (e.g., yeast, insect, or mammalian cells), after which the recombinant protein can be purified and used to generate a monoclonal or polyclonal antibody preparation that specifically binds the targeted antigen.

One of skill in the art will know how to choose an antigenic peptide for the generation of monoclonal or polyclonal antibodies that specifically bind the appropriate antigens. For example, the PredictProtein Server (www.embl-heidelberg.de/predictprotein/subunitdef.html) or an analogous program can be used to select antigenic peptides to generate antibodies suitable for use in the disclosed methods. One of skill in the art will know that the generation of two or more different sets of monoclonal or polyclonal antibodies maximizes the likelihood of obtaining an antibody with the specificity and affinity required for its intended use. The antibodies are tested for their desired activity by known methods (e.g., but not limited to, ELISA and/or immunocytochemistry) or by analogous methods. For additional guidance regarding the generation and testing of antibodies, see e.g., Harlow and Lane, Antibodies: A Laboratory Manual, Cold Spring Harbor Laboratory Press, Cold Spring Harbor, N.Y., 1988, which is incorporated by reference herein for methods of making antibodies).

The term "monoclonal antibody" as used herein refers to an antibody or antibody fragment obtained from a substantially homogeneous population of antibodies or antibody fragments, that is, the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (see, U.S. Pat. No. 4,816,567 (Cabilly et al.) and Morrison, et al., *Proc Natl Acad Sci*, 81:6851-6855 (1984)).

Monoclonal antibodies can be prepared using hybridoma methods, such as those described by Kohler and Milstein, *Nature*, 256:495 (1975), which is incorporated by reference herein for it material related to preparing monoclonal antibodies. In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro, e.g., using the Notch receptors or fragments thereof described herein.

The monoclonal antibodies may also be made by recombinant DNA methods, such as those described in U.S. Pat. No. 4,816,567 (Cabilly et al.), which is incorporated by reference herein for its material related to preparing monoclonal antibodies. DNA encoding the monoclonal antibodies of the invention can be readily isolated and sequenced using conventional procedures (for example, by using oligonucleotide probes that are capable of binding specifically to genes encoding the heavy and light chains of murine antibodies). Libraries of antibodies or active antibody fragments can also be generated and screened using phage display techniques, for example, as described in U.S. Pat. No. 5,804,440 (Burton et al.) and U.S. Pat. No. 6,096,441 (Barbas et al.), which are incorporated by reference herein for their material related to screening and preparing antibodies. Recombinant antibodies, antibody fragments, and fusions and polymers thereof can be expressed in vitro or in prokaryotic cells (e.g., bacteria) or eukaryotic cells (e.g., yeast, insect, or mammalian cells) and further purified, as necessary, using well known methods (see e.g., Sambrook, et al., Molecular Cloning: a Laboratory Manual, 3d Edition, Cold Spring Harbor Laboratory Press (2001); and Ausubel, et al., Current Protocols in Molecular Biology, John Wiley & Sons, New York, N.Y., 2001, which is updated quarterly).

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 and U.S. Pat. No. 4,342,566 (Theofilopoulos et al.). Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

Any antibody or antibody fragment useful in the methods disclosed herein, whether attached to other sequences or not, can also include insertions, deletions, substitutions, or other selected modifications of particular regions or specific amino acids residues as described herein, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. For example, amino acid sequence variants of antibodies or antibody fragments can be generated and those that display equivalent or improved affinity for antigen can be identified using standard techniques and/or those described herein. Methods for generating amino acid sequence variants are readily apparent to a skilled practitioner in the art and can include site-specific mutagenesis or random mutagenesis (e.g., by PCR) of the nucleic acid encoding the antibody or antibody fragment (Zoller, *Curr Opin Biotechnol*, 3:348-354

(1992)). Both naturally occurring and non-naturally occurring amino acids (e.g., artificially-derivatized amino acids) can be used to generate amino acid sequence variants of the antibodies and antibody fragments used in the disclosed conjugates.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods disclosed herein serves to lessen the chance that an antibody administered to a human will evoke an undesirable immune response.

The human antibodies useful in the methods disclosed herein can be prepared using any technique. Examples of techniques for human monoclonal antibody production include those described by Cole, et al. (Monoclonal Antibodies and Cancer Therapy, Alan R. Liss, p. 77, 1985) and by Boerner, et al. (*J Immunol*, 147(1):86-95 (1991)). Human antibodies (and fragments thereof) useful in the conjugates and methods disclosed herein can also be produced using phage display libraries (Hoogenboom, et al., *J Mol Biol*, 227:381 (1991); Marks, et al., *J Mol Biol*, 222:581 (1991); and Barbas, et al., Silverman, Phage Display: A Laboratory Manual, Cold Spring Harbor Laboratory Press, Cold Spring Harbor, N.Y., 2001). The references in this paragraph are incorporated by reference herein for their material related to preparing human monoclonal antibodies.

The human antibodies useful in the methods disclosed herein can also be obtained from transgenic animals. For example, transgenic mutant mice that are capable of producing a full repertoire of human antibodies in response to immunization have been described (see e.g., Jakobovits, et al., *Proc Natl Acad Sci*, 90:2551-255 (1993); Jakobovits, et al., *Nature*, 362:255-258 (1993); Bruggermann, et al., *Year in Immunol*, 7:33 (1993), which are incorporated by reference herein for their material related to preparing human monoclonal antibodies). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody), which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones, et al., *Nature*, 321:522-525 (1986); Reichmann, et al., *Nature*, 332:323-327 (1988); and Presta, *Curr Opin Struct Biol*, 2:593-596 (1992)).

Methods for humanizing non-human antibodies are well known in the art. For example, humanized antibodies can be generated according to the methods of Winter and co-workers (Jones, et al., *Nature*, 321:522-525 (1986); Riechmann, et al., *Nature*, 332:323-327 (1988); and Verhoeyen, et al., *Science*, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al), and U.S. Pat. No. 6,180,377 (Morgan et al.). The references in this paragraph are incorporated by reference herein for their material related to humanizing non-human antibodies.

Ligand Markers

In a further aspect, a marker suitable for use in the disclosed methods comprises one or more compounds chosen from a Notch receptor ligand or a Notch receptor binding fragment thereof. For example, the marker can comprises one or more Notch receptor ligands chosen from Jagged-1, Jagged-2, Delta-like-1 (D111), Delta-like-3 (D113), Delta-like-4 (D114), and fragments thereof. Nucleic acid and amino acid sequences for Jagged-1 can be found at GenBank Accession No. NM_000214 and Unigene No. Hs.409202; for Jagged-2 at GenBank Accession No. NM_002226, GenBank Accession No. NM_145159 and Unigene No. Hs.433445; for D111 at Gen Bank Accession No. NM_00561 and UniGene No. Hs.368657; for D113 at GenBank Accession No. NM_016941, GenBank Accession No. NM_0127792 and Unigene No. Hs127792; for D114 at GenBank Accession No. NM_019074 and Unigene No. Hs.458302. All of the information, including any nucleic acid and amino acids sequences, fragments or variants thereof provided for the ligands under these GenBank Accession Nos. and the Unigene Nos. are hereby incorporated in their entirety by this reference.

Other suitable Notch receptor ligands are disclosed in U.S. Pat. No. 6,703,221 (Chan et al.), which is incorporated by reference herein for its material related to Notch receptor ligands.

In addition to the Notch receptor ligands and antibodies, the marker can comprise one or more Notch receptor binding fragments. Such fragments comprise fragments of Notch receptor ligands or fragments of antibodies to Notch receptors and can comprise at least 8, 10, 12, 15, 18, 19, 20, 25, 50, 75, 100, 125, 130, 140, 150, 160, 170, 180, 190, 200, 250, 300, 350, 400, 450, 500, 550, 560, 570 or 580 contiguous amino acids from the corresponding Notch receptor ligand or Notch receptor antibody. Also included are all intermediate length fragments in this range, such as 101, 102, 103, etc.; 170, 171, 172, etc.; and 600, 601, 601, etc. The specific lengths listed herein are exemplary only and not limiting. Examples of Notch receptor binding fragments include, but are not limited to, R-JAG: CDDYYYGFGCNKFGRPRDD (SEQ ID NO:1), JAG-1: CDDYYYGFGCNKFCRPR (SEQ ID NO:2), and scrambled control peptide without agonist activity, sc-Jagged: RCGPDCFDNYGRYKYCF (SEQ ID NO:3).

Also, analogs, derivatives, and variants, as disclosed herein, of Notch receptor ligands and/or Notch receptor binding fragments can be used as markers in the disclosed methods. Such analogs and variants can have from about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homology to a given Notch receptor ligand sequence or Notch receptor binding fragment sequence.

These and other suitable Notch receptor ligands and Notch receptor binding fragments can be obtained from commercial sources or can be synthesized by peptide synthesis methods known in the art. One method of producing the disclosed Notch receptor ligands and Notch receptor binding fragments is to link two or more peptides together by protein chemistry techniques. For example, peptides can be chemically synthesized using currently available laboratory equipment using either Fmoc (9-fluorenylmethyloxycarbonyl) or Boc (tert-butyloxycarbonyl) chemistry (Applied Biosystems, Inc., Foster City, Calif.). One skilled in the art can readily appreciate that a peptide corresponding to a Notch receptor ligand or Notch receptor binding fragment can, for example, be synthesized by standard chemical reactions. For example, a peptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant, Synthetic Peptides: A User Guide, W.H. Freeman and Co., NY (1992); Bodansky and Trost, Ed., Principles of Peptide Synthesis, Springer-Verlag Inc., NY (1993), which are incorporated by reference herein for their material related to peptide synthesis). Alternatively, the peptide can be independently synthesized in vivo as described herein. Once isolated, these independent peptides can be linked to form a peptide or fragment thereof via similar peptide condensation reactions.

For example, enzymatic ligation of cloned or synthetic peptide segments allow relatively short peptide fragments to be joined to produce larger peptide fragments, polypeptides, or whole protein domains (Abrahmsen, et al., *Biochemistry*, 30:4151 (1991)). Alternatively, native chemical ligation of synthetic peptides can be utilized to synthetically construct large peptides or polypeptides from shorter peptide fragments. This method comprises a two step chemical reaction (Dawson, et al., *Science*, 266:776-779 (1994), which is incorporated by reference herein for its material related to peptide synthesis). The first step comprises the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini, et al., *FEBS Lett*, 307:97-101 (1992); Clark-Lewis, et al., *J Biol Chem*, 269:16075 (1994); Clark-Lewis, et al., Biochemistry, 30:3128 (1991); Rajarathnam, et al., *Biochemistry*, 33:6623-30 (1994), all of which are incorporated by reference herein for their material related to peptide synthesis).

Alternatively, unprotected peptide segments can be chemically linked where the bond formed between the peptide segments as a result of the chemical ligation is an unnatural (non-peptide) bond (Schnolzer, et al., *Science*, 256:221 (1992), which is incorporated by reference herein for its material related to peptide synthesis). This technique has been used to synthesize analogs of protein domains as well as large amounts of relatively pure proteins with full biological activity (deLisle Milton, et al., Techniques in Protein Chemistry IV. Academic Press, New York, pp. 257-267 (1992), which is incorporated by reference herein for its material related to peptide synthesis).

Detectable Moiety

Any of the markers disclosed herein can be labeled with a detectable moiety. A detectable moiety is a molecule or molecule fragment that can be associated with a marker and used to identify, separate, sort, or isolate. One or a plurality of the same or different detectable moieties can be associated with any given marker. By detecting a detectably moiety associated with a marker, one can detect the cell that the marker is bound to.

The detectable moiety can be directly or indirectly associated with the marker. "Directly or indirectly associated" will be understood by one skilled in the art to include various methods for associating a detectable moiety with a marker. For example, a marker to be detected by can be coupled to biotin, have one or more free amine groups, or have one or more free sulfhydryl groups. These various detectable moieties can respectively be detected by, for example, associating them with additional detectably moieties such as microspheres that have been coated with strepavidin, maleimide, or that have been carboxylated. By detecting the second detectable moieties (in this example, the microspheres), one can "indirectly" detect the first detectable moiety (e.g., the biotin, free amine, or free sulfhydryl), and thus detect the marker. As another example, a fluorescent or radioactive compound can be incorporated into the marker and the fluorescence or radioactivity directly detected. Alternatively, a first detectable moiety can be associated with a second detectable moiety, which can then be associated with a third detectably moiety and so on.

Useful detectable moieties include, for example, sortable components, fluorescent molecules, radiolabels, enzymes, and dyes.

Sortable components include molecules and compositions that can be specifically bound or that can selectively interact with other molecules and compounds. Examples include beads or particles, such as paramagnetic bead or functionalized microspheres, that can be separated based on a property of the bead or particle. Thus, for example, cells that are directly or indirectly associated with a paramagnetic bead or particle can be selected or separated by magnetic sorting. Similarly, a variety of types of microspheres can be used. See, e.g., WO 99/19515 and WO 99/37814, which are incorporated herein for their material related to types of microspheres and methods of making and using same.

Fluorescent molecules are particularly useful for fluorescence activated cell sorting (FACS). Examples of fluorescent labels that can be used to label the markers disclosed herein include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY™, Cascade Blue™, Oregon Green™, pyrene, lissamine, xanthenes, acridines, oxazines, phycoerythrin, macrocyclic chelates of lanthanide ions such as Quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels that can be used as tag components include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.18, CY5.18, CY7, Dans (1-Dimethyl Amino Naphaline 5 Sulphonic Acid), Dansa (Diamino Naphtyl Sulphonic Acid), Dansyl NH—$CH_3$, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC. The choice of a detection moiety is capable of being made by one skilled in the art and will depend on such factors as the particular precursor cell, the particular marker, the particular cell sample, the type detection apparatus, convenience, cost, and the like.

Examples of radiolabels include, but are not limited to, moieties that contain $^3H$, $^{125}I$, $^{35}S$, $^{14}C$, and $^{32}P$. Examples of enzymes include, but are not limited to, LacZ, CAT, horse radish peroxidase, alkaline phosphatase and others commonly used as detectable enzymes either in an EIA or in an ELISA.

Linking a detectably moiety to a marker disclosed herein can be readily accomplished using techniques generally known to those of skill in the art. The starting materials and reagents used in preparing these conjugates are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Molecular Probes (Eugene, Org.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

In one example, the marker is coupled or linked to the detectable moiety via a reactive chemical group on the marker and/or the detectable moiety such that the coupling between the marker and the detectable moiety results in a covalent bond between the two that is resistant to reducing agents. Reactive chemical groups include, e.g., sulfhydryl groups, hydroxyl groups, amino groups, carboxyl groups, and imidazole groups. The reactive chemical group can be in the hinge region of an antibody marker. This location reduces or eliminates interference between the marker-antibody and antigen interaction.

The coupling of the marker to the detectable moiety can also involve an activating agent. Various activating agents that can be used for the coupling reaction include, but are not limited to, 1-ethyl-3-(3-dimethylaminopropyl) carbodiimide (EDC), dicyclohexylcarbodiimide (DCC), N,N'-diisopropyl-carbodiimide (DIP), benzotriazol-1-yl-oxy-tris-(dimethylamino)phosphonium hexa-fluorophosphate (BOP), hydroxybenzotriazole (HOBt), and N-methyhnorpholine (NMM), including mixtures thereof. The coupling reaction can be carried out in solvents such as N-methylpyrrolidone (NMP) or in DMF.

The choice of a detectable moiety is capable of being made by one skilled in the art and will depend on such factors as the particular cell to be detected, the particular cell sample, convenience, preference, costs, and the like.

Targeting Molecule

The disclosed markers can be conjugated to a targeting molecule. A targeting molecule is a molecule that facilitates the localization of the marker to cells and tissues for which the targeting molecule is designed to target. A suitable targeting molecule for the disclosed methods includes, but is not limited to, an antibody or antibody fragment, a ligand, or binding fragment thereof. For example, an antibody or antibody fragment that is specific for a particular cell, e.g., a precursor cell, can be conjugated to a marker.

One or more targeting molecules can be used with any given marker. It is also possible for the targeting molecule to be specific for other cell surface proteins besides a Notch receptor. For example, a targeting molecule that is specific for cell surface proteins such as, for example, FGF7, FGF10, or Shh, can be conjugated to a marker that specifically binds to a Notch receptor.

The choice of a targeting molecule is capable of being made by one skilled in the art and will depend on such factors as the particular cell to be targeted, the particular cell sample, convenience, and the like.

The targeting molecule-marker conjugates disclosed herein can be readily synthesized using techniques generally known to those of skill in the art. The starting materials and reagents used in preparing these conjugates are either available from commercial suppliers or can be prepared using standard techniques as described above for the detectably moieties. In one example, the marker is coupled or linked to the targeting molecule via a reactive chemical group on the marker and/or the targeting molecule such that the coupling between the marker and the targeting molecule results in a covalent bond between the two that is resistant to reducing agents. Reactive chemical groups include, e.g., sulfhydryl groups, amino groups, carboxyl groups, and imidazole groups. The reactive chemical group can be in the hinge region of an antibody targeting molecule and/or marker. This location reduces or eliminates interference between the antibody/antigen interaction and the marker.

As discussed above for the detectably moiety, the coupling of the marker to the targeting molecule can also involve an activating agent, such as those disclosed above.

Detecting/Identifying

As disclosed herein, the marker binds to all or a portion of a Notch receptor, which is expressed by a precursor cell, and detection of the marker thus indicates a precursor cell. Detecting the bound marker can be performed by methods known in the art. For example, detecting the bound marker can involve optical analysis, fluorescence analysis (e.g., FACS), or immunohistochemical techniques, immunobased assays (e.g., ELISA). Detection of the bound marker can also be accomplished with chromatography (e.g., thin-layer, column, gas, high performance liquid, ion exchange, ion pair) or electrophoresis (e.g., gel, SDS-PAGE). While not necessary, a detection moiety on the marker can allow efficient detection of the bound marker.

The precursor cell can be isolated by identifying the precursor cell and separating the identified cell from a cell sample. Identifying the precursor can be accomplished by the methods disclosed herein, for example, by contacting a cell sample with a marker that selectively binds a Notch receptor or its ligands. The identified cell can be separated from the cell sample by methods known in the art. For example, the cell sample can be passed through a cell sorter. Alternatively, the cell sample can be passed through a column that is functionalized so that it is selective for the identified cell.

Also disclosed are precursor cells, such as a pancreatic precursor cell, identified and isolated by the disclosed methods.

Methods of Stimulating Differentiation

In a further aspect, disclosed herein are methods of stimulating differentiation of a pancreatic precursor cell comprising contacting the pancreatic precursor cell with one or more compounds chosen from a Notch receptor ligand, a Notch receptor binding fragment, and an agent that modulates Notch receptors. Suitable Notch receptor ligands are as disclosed above for markers and include, but are not limited to, Jagged-1, Jagged-2, Delta-like-1 (Dl11), Delta-like-3 (Dl13), and Delta-like-4 (Dl14), and Notch receptor binding fragments thereof.

An agent that modulates a Notch receptor is any agent that increases, decreases, inhibits, or promotes Notch signaling, including, for example, transcription factors, morphogen factors, growth factors, and the like. Examples of such agents include, but are not limited to, GLP-1 and exendin-4, epidermal growth factor, nicotinamide, gastrin, hepatocyte growth factor, and the like.

The compounds used to contact the pancreatic precursor cells to stimulate differentiation can be conjugated to a targeting molecule as described herein.

A pancreatic precursor cell can be obtained by the identification and isolation methods disclosed herein.

The pancreatic precursor cell can be contacted in vivo or ex vivo. The pancreatic precursor cell can be contacted by one or more compounds disclosed herein by submerging or immersing the cell in a solution containing the compound. In another example, the pancreatic precursor cell can be coated or sprayed with a solution containing the compound. In still another example, the pancreatic precursor cell can be contacted with a medium, such as a growth medium, that contains the compound. The various methods of contacting the pancreatic precursor cell with the compounds disclosed herein will be readily apparent to one of ordinary skill in the art, depending on such factors as the type of cell, tissue, organ, or subject, the particular compound to be used, convenience, and the like. In a further aspect, a pancreatic precursor cell can be contacted with an agent that increases intracellular cAMP levels in the cell, such as one or more of IBMX or GLP-1.

After contacting the pancreatic precursor cell with the compounds disclosed herein, the pancreatic precursor cell can differentiate into, for example, an β-cell or a β-cell. Also, contacting the pancreatic precursor cell with the compounds disclosed herein can stimulate differentiation into a cell that produces insulin, glucagon, or a mixture thereof. Such differentiated cells can be utilized, for example, in islet cell replacement therapy.

Methods of Increasing Insulin Release and Methods of Improving Pancreatic Endocrine Function In yet a further aspect, disclosed herein are methods of increasing insulin synthesis from a pancreatic β-cell comprising contacting the β-cell with one or more compounds chosen from a Notch receptor ligand, a Notch receptor binding fragment, and an agent that modulates Notch receptors. These methods are also useful for increasing intracellular insulin and insulin release.

Also disclosed herein are methods of improving pancreatic endocrine function comprising contacting a pancreatic β-cell with one or more compounds chosen from a Notch receptor ligand, Notch receptor binding fragment, and an agent that modulates Notch receptors. Improvements in pancreatic endocrine function can be determined, for example, by measuring insulin secretion, synthesis, or function (e.g., blood glucose levels); intracellular insulin content, physiologic insulin secretion (1st and 2nd phase), or proinsulin to insulin ratio.

Suitable pancreatic β-cells can be obtained for in vitro methods by the identification, isolation, and differentiation of a pancreatic precursor cell by the methods disclosed herein. Alternatively, the pancreatic β-cell can be obtained from other sources. For example, pancreatic β-cells can be obtained from a subject or from a commercial supplier. In one example, pancreatic β-cells can comprise part of an islet-like cluster. In another example, pancreatic β-cells can be isolated from a subject (e.g., a human) with diabetes. In still another example, pancreatic β-cells can be in an intact islet intended for transplantation into an insulin dependent diabetic subject. β-cells can also be in an immature, not fully differentiated cell in vitro or in vivo. In other examples, β-cells can be formed from the differentiation of mammalian embryonic stem cells, bone marrow cells, blood cord cells, adult pancreatic cells, hepatic cells, or other stem cells within an adult organ.

Obtaining pancreatic β-cells from differentiated of stem cells can be achieved by isolating adult stem cells from the adult pancreas. For this, a whole human pancreas can be digested using dispase and collagenase and the resultant endocrine and exocrine tissue can be subcultivated from this. In this tissue is ductal tissue containing proendocrine cells. These can be induced to form immature clusters of endocrine cells using factors that have been reported previously in the scientific and patent literature including, but not limited to, GLP-1 receptor agonists, epidermal growth factor, nicotinamide, gastrin, hepatocyte growth factor, and the like.

The β-cell can be contacted with one or more compounds disclosed above. For example, the compound can be a Notch receptor ligand, such as, but not limited to, Jagged-1, Jagged-2, Dl11, Dl13, and Dl14. The compound can be a Notch receptor binding fragment derived from Jagged-1, Jagged-2, Dl1, Dl13, and Dl14. Also, the compound can be an agent that modulates the Notch receptor (e.g., GLP-1 and exendin-4). One or more of these compounds in any combination can be contacted to the β-cell. Further, one or more of these compounds can be conjugated to a targeting molecule, as described herein.

The β-cell can be contacted with the disclosed compounds in a manner like that disclosed above for differentiation of precursor cells. For example, the β-cell can be contacted in vivo or ex vivo with the disclosed compounds.

As these disclosed compounds, such as Jagged, have the ability to increase insulin synthesis by transcriptional upregulation of the insulin gene and increase the integral β-cell proteins IRS2 and PDX-1, treatment of these immature endocrine clusters would enhance their ability to perform as fully differentiated endocrine cells and thus make them more suitable for use in clinical implantation.

Methods for Treating a Subject with a Metabolic Disease and Preventing the Onset of a Metabolic Disorder in a Subject Also disclosed herein are methods of treating a subject with a metabolic disease comprising administering to the subject an effective amount of one or more compounds chosen from a Notch receptor ligand, a Notch receptor binding fragment, and an agent that modulates Notch receptors. Further disclosed are methods of delaying or preventing the onset of a metabolic disorder in a subject, comprising administering to a subject at risk for the metabolic disorder an effective amount of one or more of a Notch receptor, Notch receptor binding fragment, or an agent that modulates the Notch receptor.

By "metabolic disease" or "metabolic disorder" is meant an impairment of the normal state of a subject or one of its parts that interrupts or modifies the performance of processes by which a particular substance is handled (as by assimilation and incorporation or by detoxification and excretion) in the subject or one of its parts and can be a response to environmental factors (e.g., malnutrition, industrial hazards, climate, injury), to infective agents (e.g., bacteria, fungus, or viruses), to inherent defects of the organism (e.g., genetic anomalies), or to combinations of these factors. In one example, the metabolic disease or disorder can be diabetes.

Compositions used for treating, preventing, or delaying the onset of a metabolic disorder include any of the compounds disclosed herein. For example, the compounds can be a Notch receptor ligand, Notch receptor binding fragment, or the agent that modulates the Notch receptor. The Notch receptor ligands that can be used include one or more Notch receptor ligands chosen from Jagged-1, Jagged-2, delta-like-1, delta-like-3, or delta-like-4, or a fragment thereof. Optionally, these compounds can be conjugated to a targeting molecule such as an antibody.

By the phrase "effective amount" of a compound is meant a nontoxic but sufficient amount of a compound to provide the desired result, e.g., modulation, inhibition, treatment, or prevention. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

Generally, the dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject in need of attention for the treatment of diabetes or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved (e.g., insulin release is increased), 2) the progression of the disease or condition is shown to be stabilized, or slowed, or reversed, or 3) the need for other medications for treating the disease or condition is lessened or obviated, then a particular treatment regimen will be considered efficacious.

Any of the compounds disclosed herein can be used therapeutically in combination with a pharmaceutically acceptable carrier. In another example, any of the compounds disclosed herein can be used prophylactically, i.e., as a preventative agent, with a pharmaceutically acceptable carrier. The compounds described herein can be conveniently formulated into pharmaceutical compositions composed of one or more of the compounds in association with a pharmaceutically acceptable carrier. See e.g., Remington's Pharmaceutical Sciences, latest edition, by E.W. Martin Mack Pub. Co., Easton, Pa., which discloses typical carriers and conventional methods of preparing pharmaceutical compositions that can be used in conjunction with the preparation of formulations of the compounds described herein and which is incorporated by reference herein. Such pharmaceutical carriers, most typically, would be standard carriers for administration of compositions to humans and non-humans, including solutions such as sterile water, saline, and buffered solutions at physiological pH. Other compounds will be administered according to standard procedures used by those skilled in the art. The pharmaceutical compositions described herein can include, but are not limited to, carriers, thickeners, diluents, buffers, preservatives, surface active agents and the like in addition to the molecule of choice. Pharmaceutical compositions can also include one or more additional active ingredients such as antimicrobial agents, antiinflammatory agents, anesthetics, and the like.

The compounds and pharmaceutical compositions described herein can be administered to the subject (e.g., a human) in a number of ways depending on whether local or systemic treatment is desired, and on the area to be treated. Thus, for example, a compound or pharmaceutical composition described herein can be administered as an oral tablet and/or injectable solution. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein for its teaching of sustained release systems.

In one example, the administration is by injection. Preparations for injection administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives, such as antimicrobials, anti-oxidants, chelating agents, and inert gases and the like, can also be present.

In one example, the administration is by oral administration. Compositions for oral administration can include powders or granules, suspensions or solutions in water or non-aqueous media, capsules, sachets, or tablets. Thickeners, flavourings, diluents, emulsifiers, dispersing aids or binders can be desirable.

Compositions comprising the pharmaceutically acceptable carriers disclosed herein and the Notch ligand, Notch receptor binding fragments, and/or agent that modulates Notch receptors can be conjugated to a targeting molecule (e.g., antibody), as disclosed herein. Also, the compositions can also contain anti-diabetic therapeutic agents. Suitable anti-diabetic therapeutic agents include, but are not limited to, Acetohexamide; Buformin; Butoxamine Hydrochloride; Camiglibose; Chlorpropamide; Ciglitazone; Englitazone Sodium; Etoformin Hydrochloride; Gliamilide; Glibomuride; Glicetanile Sodium; Glifumide; Glipizide; Glucagon; Glyburide; Glyhexamide; Glymidine Sodium; Glyoctamide; Glyparamide; Insulin; Insulin, Dalanated; Insulin Human; Insulin Human, Isophane; Insulin Human Zinc; Insulin Human Zinc, Extended; Insulin, Isophane; Insulin Lispro; Insulin, Neutral; Insulin Zinc; Insulin Zinc, Extended; Insulin Zinc, Prompt; Linogliride; Linogliride Fumarate; Metformin; Methyl Palmoxirate; Palmoxirate Sodium; Pioglitazone Hydrochloride; Pirogliride Tartrate; Proinsulin Human; Seglitide Acetate; Tolazamide; Tolbutamide; Tolpyrramide; Troglitazone; Zopolrestat.

EXAMPLES

The following examples are put forth so as to provide those of ordinary skill in the art with a complete disclosure and description of how the methods, processes, polypeptides, nucleic acids, and/or compositions claimed herein can be made and evaluated, and are intended to be purely exemplary of the disclosed subject and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of conditions, e.g., component concentrations, desired solvents, solvent mixtures, temperatures, pressures, and other ranges and conditions that can be used to optimize the methods described herein. Only reasonable and routine experimentation will be required to optimize such process conditions.

Example 1

By RT-PCR, all four Notch genes are expressed in both rodent and human isolated islets. However, Notch-3 was not found in a clonal β-cell line (RIN 1046-38) leading to the conclusion that the Notch-3 in islets may be from vascular endothelium or its absence is pathognomonic of insulinomas (FIG. 1A). Notch ligands, Jagged-1, Jagged-2 and Delta-1 were also expressed in islets and RIN cells, while Delta-3 was absent from human and Delta-4 was absent from rodent islets (for positive controls see FIG. 6). Using an antibody specific to the C-terminus of the Notch-1 receptor (recognizing all intracellular fragments), Notch-1 was present in all endocrine cells of adult fasted rat and human islets (FIG. 1B) and by double-labelled immunohistochemistry co-localised with both insulin and glucagon. While it was absent in nuclei of the rat islet cells, it was present in many nuclei in human islets (FIG. 1B). Jagged-1 was present in all islet cells (and ducts) and it was clearly membrane-associated in RIN cells (FIG. 1C). Delta-1 localization in islets was similar to Jagged-1.

Figure 2:
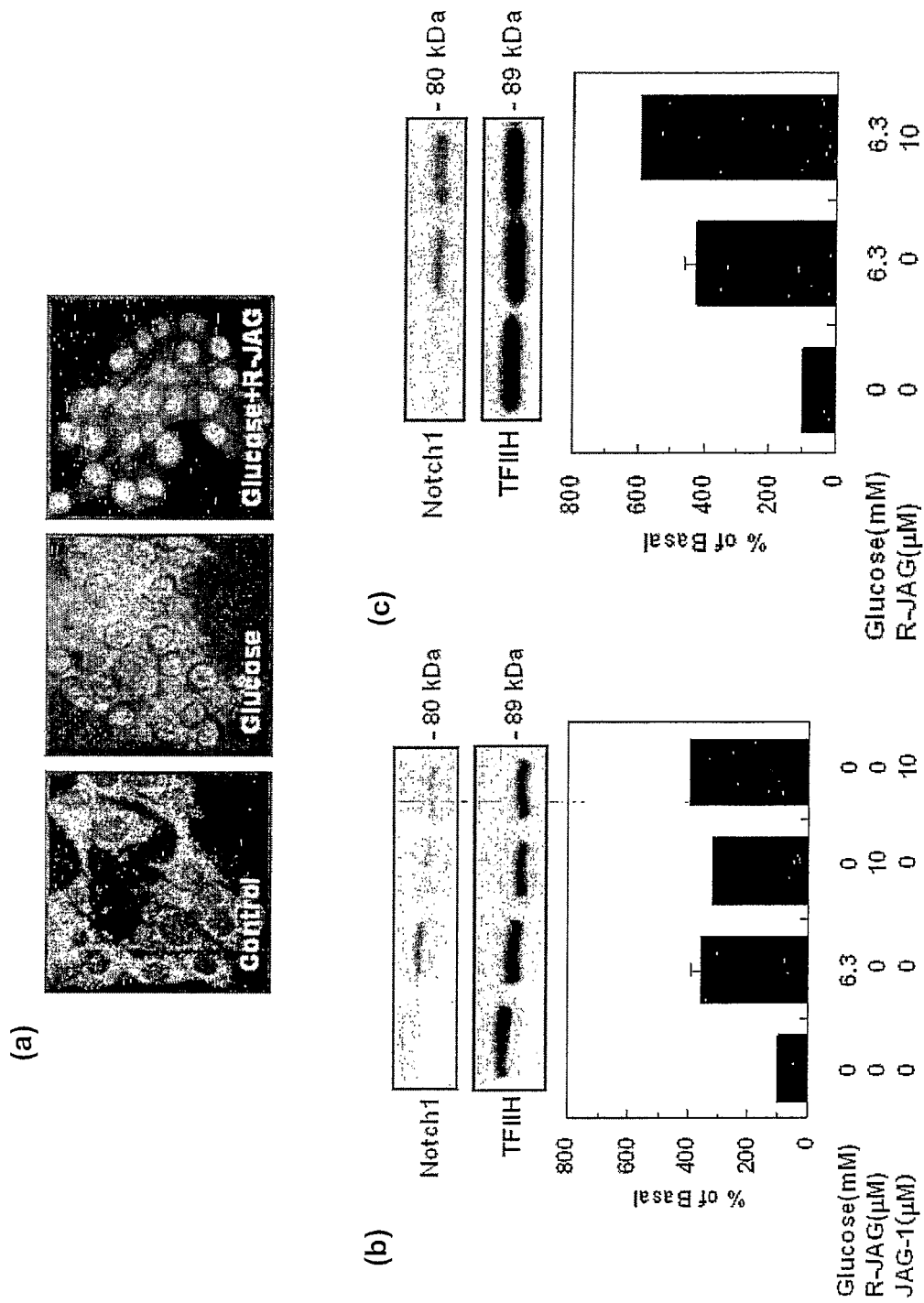
FIGS. 2A-C show that Notch is activated by glucose and Jagged-related peptides in RIN cells.

NICD was detected at low levels in nuclei of unstimulated RIN cells (i.e., not being induced to secrete insulin) as shown by indirect immunofluorescence and immunoblotting of nuclear extracts (FIGS. 2A [control], B and C). In contrast, glucose-stimulated cells showed a 4-fold increase in nuclear localisation of NICD (FIGS. 2A, B and C). Cells treated with the Jagged-related peptides R-JAG and JAG-1 (Nickoloff, et al., *Cell Death Differ*, 9:842-855 (2002)) (corresponding to Jagged residues 188-204, highly conserved between Jagged-1 and -2) stimulated a 4-fold increase (in the absence of glucose), in NICD translocation (FIG. 2B). R-JAG and glucose together caused a 6-fold increase above control levels in NICD nuclear localization (FIGS. 2A and C).

Figure 3:
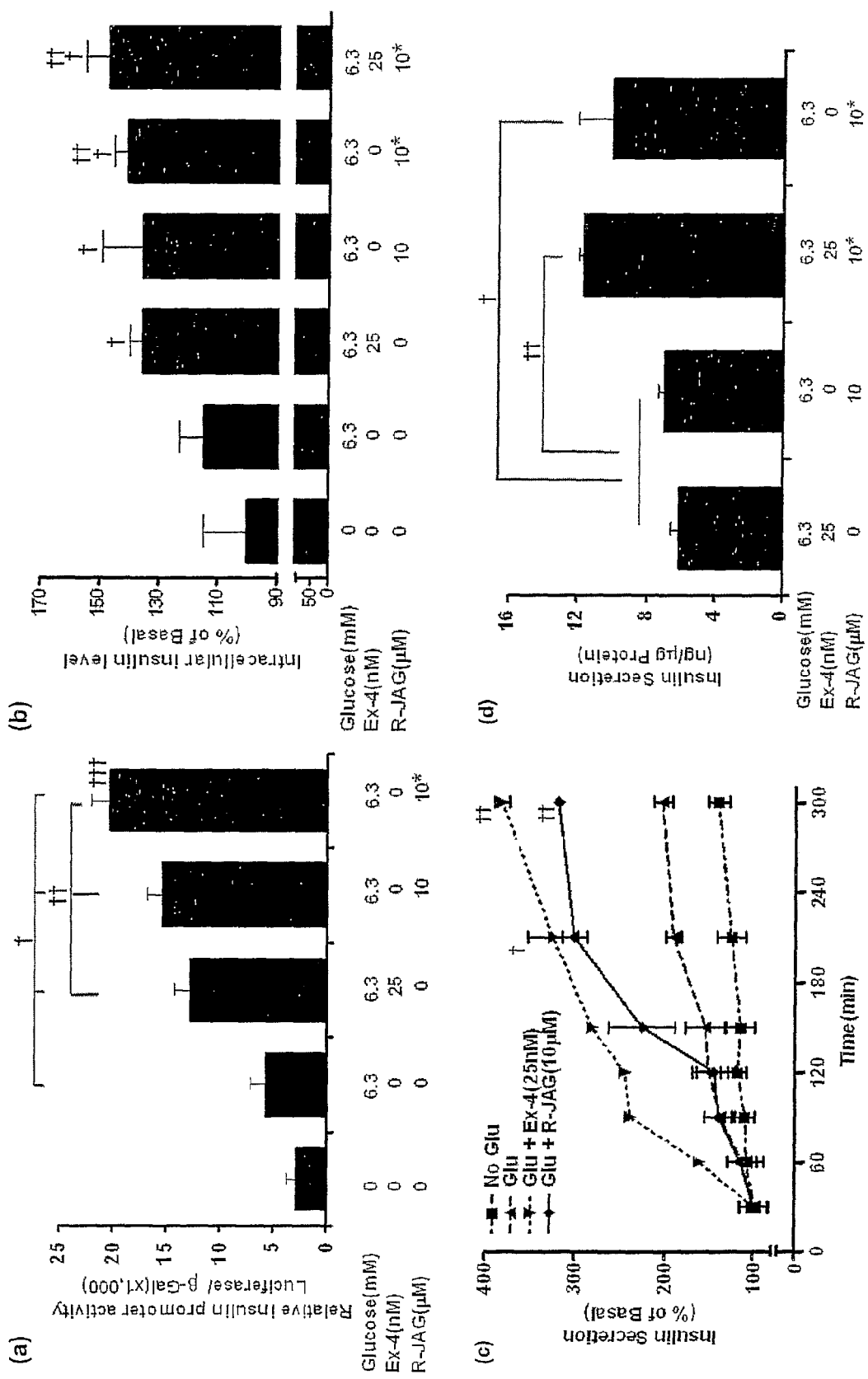
FIGS. 3A-D show that R-JAG and Exendin-4 (Ex-4) increase insulin release by transcriptional upregulation of insulin gene in RIN cells.

Because NICD is a transcriptional regulator, the effect of R-JAG and JAG-1 treatment on the prototypic function of β-cells i.e., transcription of insulin was investigated next. As both peptides gave similar findings, the results from just one peptide, R-JAG, are shown. RIN cells were transfected with a plasmid encoding the rat insulin 1 promoter linked to a luciferase reporter gene (Ins-1-luc plasmid). Addition of R-JAG every two hours for a total of 6 h resulted in a 4-fold increase in insulin promoter activity above that seen with glucose treatment alone (FIG. 3A) and increased insulin mRNA levels (FIG. 7). The transcriptional upregulation of the insulin gene resulted in a significant increase in total intracellular insulin (FIG. 3B). R-JAG treatment led to elevated insulin release into the medium after 2.5 h had elapsed, consistent with increased constitutive insulin release as a result of increased synthesis. In a concentration range of 5-100 μM, 10 and 20 μM R-JAG gave maximum insulin release (FIG. 3C). The cells continued to exclude trypan blue, indicating cell death was not responsible for increasing insulin levels in the medium. Replenishment of R-JAG every two hours had a greater effect on insulin secretion than a single treatment of R-JAG, probably because of degradation of the single-dose peptide (FIG. 3D).

Figure 4:
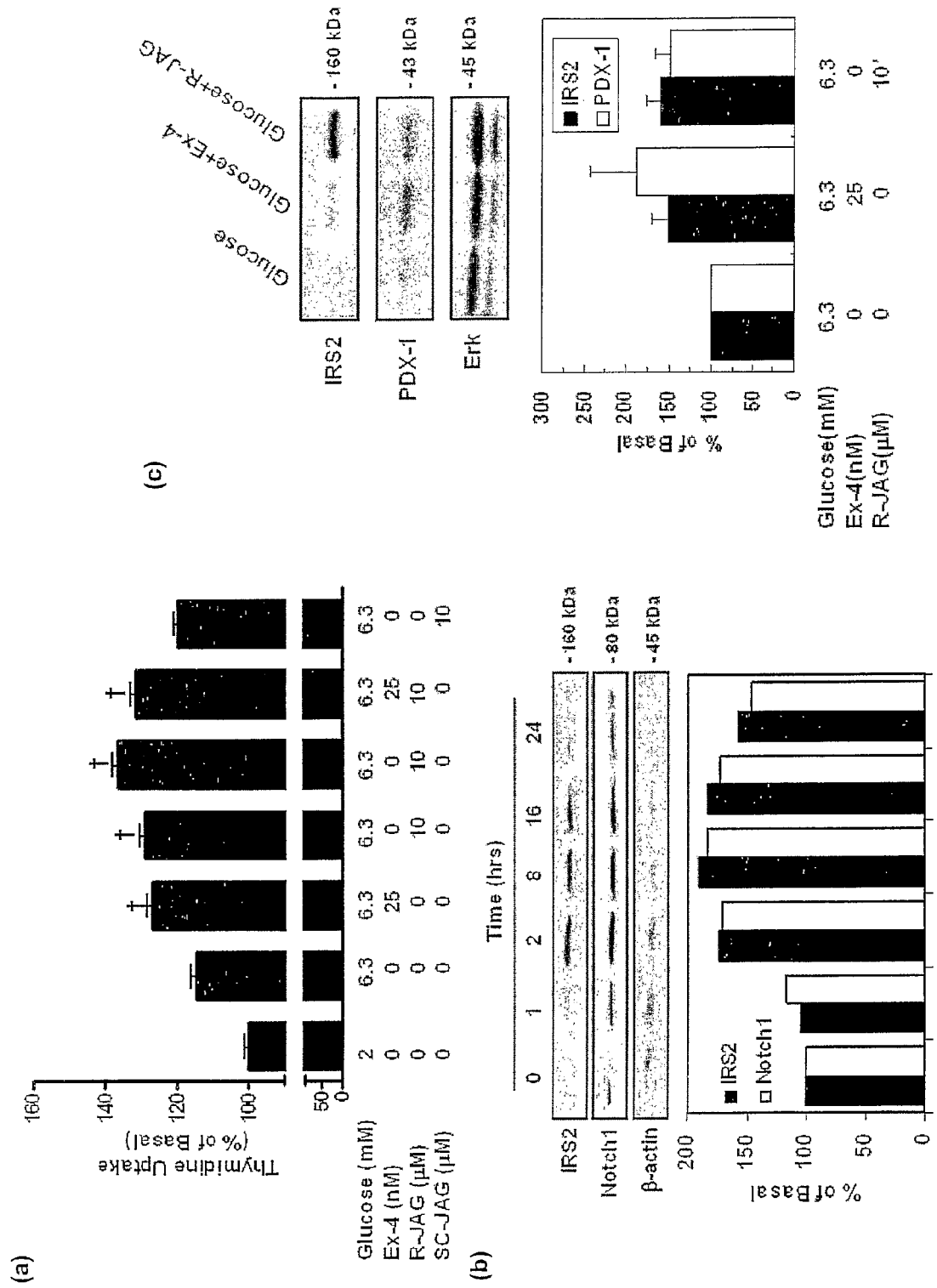
FIGS. 4A-C show R-JAG and Exendin-4 (Ex-4) treatment increase β-cell proliferation and upregulate IRS2 and PDX-1 protein levels.
Figure 9:
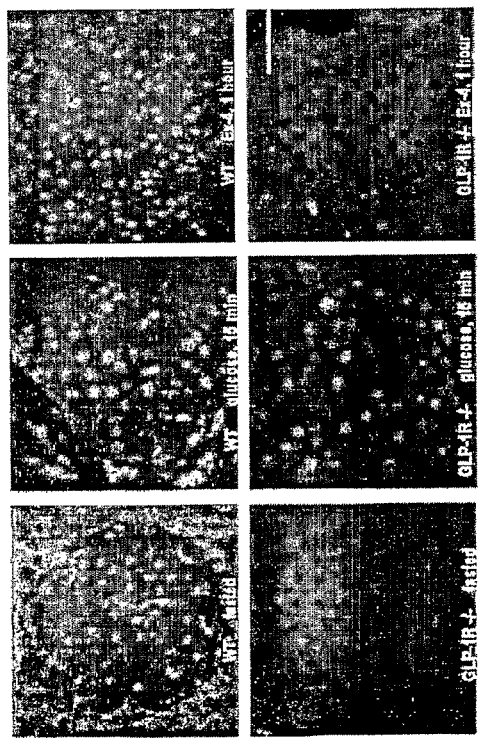
FIG. 9 shows indirect immunofluorescence for the intracellular region of Notch-1 (NICD) in GLP-1R null and wild-type mice, fasted and treated with intraperitoneal glucose and/or Ex-4. Fasted wild-type mice had NICD in some islet nuclei, but fasted null mice appeared to have little or no NICD in islet nuclei. Glucose increased NICD in islet nuclei in both groups of mice, while Ex-4 increased NICD in all islet cells of wild-type animals only. Scale bar represents 75 μm.

Pharmacological doses of GLP-1 receptor (GLP-1R) ligands have effects in islets reminiscent of those shown above with Jagged-related peptides. GLP-1 is an incretin hormone secreted from enteroendocrine cells in response to food, and GLP-1R is a specific G-protein coupled receptor, engagement of which leads to increased intracellular cAMP-dependent protein kinase A (PKA) activation, resulting in increased insulin secretion in a glucose dependent manner (Doyle and Egan, *Rec Prog Hormone Res*, 56:377-99 (2001)). GLP-1 analogues and Exendin-4 (Ex-4) are potential candidates for treating type-2 diabetes because of their acute insulinotropic effects, promotion of insulin gene expression (demonstrated again, FIG. 3A) and insulin biosynthesis, and trophic effects on islets (Holst, *Diabetes Metab Res Rev*, 18:430-441 (2002)). Ex-4, unlike R-JAG, acutely increased insulin secretion into the medium, as expected, and, similar to R-JAG, it continued to increase insulin release (FIG. 3C) because of its known effects on insulin biosynthesis (FIG. 3B). The effects of R-JAG and Ex-4 together were greater that either alone by the 6 h time point (FIG. 3D).

β-cell proliferation was next investigated by measuring [$^3$H]thymidine uptake in RIN cells following 8 h treatment with R-JAG as Notch is known to regulate cell cycle events. Thymidine uptake was increased by 30% above that of glucose treatment, whereas the scrambled Jagged peptide had no effect (FIG. 4A). This finding implicates IRS-2 activation by Notch as IRS-2, an insulin/IGF-1 signalling protein, is essential for β-cell function, growth, survival, and expansion (Withers, et al., *Nature*, 391:900-904 (1998) and Hennige, et al., *J Clin Invest*, 112:1521-1532 (2003)). R-JAG increased IRS-2 mRNA (FIG. 7) and protein levels in RIN cells (FIG. 4B), and when mouse islets of Langerhans were treated with R-JAG for 8 h, there was a 1.5-fold increase in IRS-2 protein levels (FIG. 4C). R-JAG treatment also increased total Notch1 levels (FIG. 4B, described previously in murine erythroleukemia cells (Jang, et al., *J Cell Physiol*, 199:418-33 (2004)). PDX-1, a transcription factor necessary for β-cell differentiation, regulates insulin, GLUT2, glucokinase and islet amyloid polypeptide gene expression in differentiated β-cells (Habener, J. F., *Drug News Perspect*, 15:491-497 (2002)). It is down-stream of IRS-2 activation (Kitamura, et al., *J Clin Invest*, 110: 1839-1847 (2002)). As with IRS2, PDX-1 levels were increased by R-JAG in islets (FIG. 4C) and RIN cells (FIG. 8). As shown previously, GLP-1R activation by Ex-4 increased β-cell proliferation and total intracellular insulin (Holst, *Diabetes Metab Res Rev*, 18:430-441 (2002)). (FIGS. 4A and B) and protein levels of IRS-2 (Jhala, et al., *Genes & Dev*, 17:1575-1580 (2003)) and PDX-1 (Wang, et al., *Endocrinology*, 142:1820-1827 (2001)) (FIG. 4C and FIG. 9).

Figure 5:
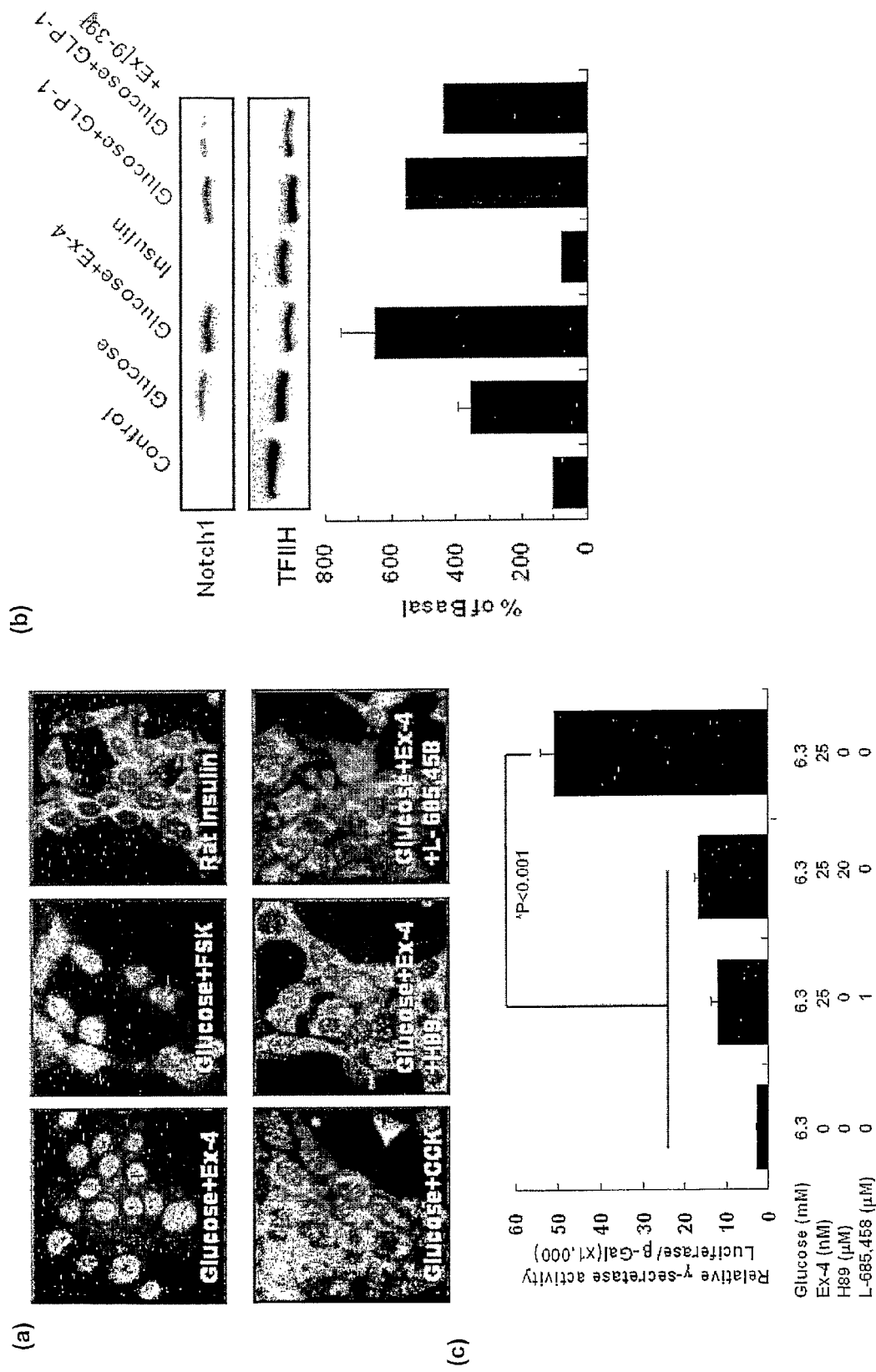
FIGS. 5A-C show that Exendin-4 (Ex-4) in RIN cells causes NICD translocation in a PKA- and γ-secretase dependent manner, and processing of transfected Notch ΔE-GFP is sensitive to Ex-4, which is abrogated by γ-secretase and PKA inhibitors.

Because the data suggested that Ex-4 and R-JAG have similar regulatory effects on β-cell function, whether GLP-1R signalling interacts with Notch was investigated. It was found that Ex-4 and GLP-1 were even more effective than R-JAG, increasing NICD nuclear localization as much as 7.5-fold in the presence of glucose (FIGS. 5A and B). This was receptor specific as treatment with GLP-1 (50 nM), in conjunction with the GLP-1R antagonist Exendin 9-39 (Ex [9-39], 500 nM) (Wang, et al., *J Clin Invest*, 99:2883-2889 (1997)), was equivalent to glucose treatment alone (FIG. 5B). In vivo studies also showed that Ex-4 (1 nmol/kg), given intraperitoneally (IP), caused NICD translocation to nuclei of practically all islet cells in wild-type mice but not in GLP-1R null mice (Scrocchi, L. A. et al. *Nat. Med.*, 2:1254-1258 (1996)) (FIG. 9). Glucose (1 g/kg, IP) also induced NICD translocation in some islet cells of both wild-type and null mice.

Figure 10:
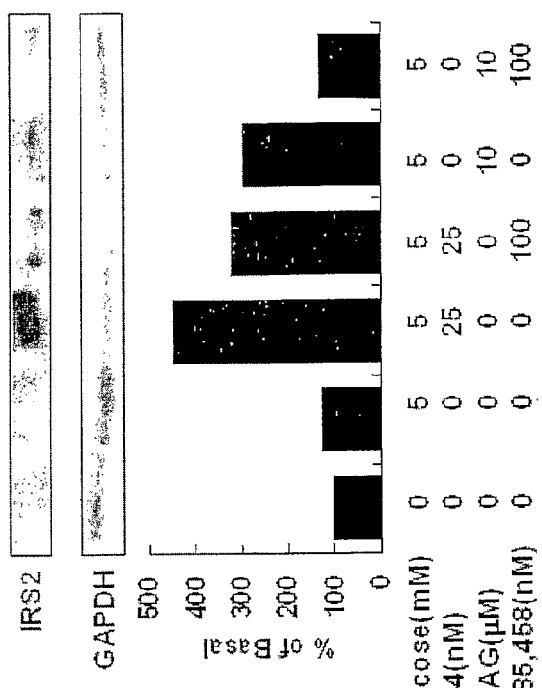
FIG. 10 shows one representative immunoblot for C57/ BL6 mouse islets treated for 8 h with glucose, Ex-4 or R-JAG, in the presence or absence of γ-secretase inhibitor L-685,458. R-JAG-mediated increases in IRS2 levels were completely abrogated by L-685,458. The 4.5-fold increase in IRS2 levels by Ex-4 was decreased by L-685,458. Ex-4 also increases IRS2 levels by a CREB-mediated induction of IRS2, and this component of Ex-4 signalling would not be expected to be prevented by L-685,458 (relative amounts of IRS2 protein normalized to GAPDH levels).
Figure 11:
FIG. 11 shows indirect immunofluorescence demonstrates the presence of presenilin-1 (PSI) in RIN cells. The mouse monoclonal antibody was against the C-terminus PSI (Chemicon; 1:50). The secondary antibody was an AlexaFluor488 rabbit anti-mouse (1:1,000).

The adenylyl cyclase activator forskolin increased nuclear NICD (FIG. 5A), and the response to exogenous insulin was equivalent to control samples, indicating that endogenous insulin release was not the cause of NICD translocation (FIGS. 5A and B). Cholecystokinin (CCK), which increases insulin secretion in a non-cAMP dependent manner, also did not increase NICD translocation above that seen with glucose alone (FIG. 5A). The PKA inhibitor H89 (10 µM, a concentration shown to abrogate Ex-4-mediated insulin secretion (Wang, et al., *Endocrinology*, 142:1820-1827 (2001)) diminished Ex-4-mediated translocation of NICD (FIG. 5A). In addition, H89 prevented glucose-mediated NICD translocation. There is no report in the literature that phosphorylation effects the efficiency of NICD translocation; therefore, it was not hypothesized that phosphorylation of NICD by PKA is a mechanism by which GLP-1R ligands activate translocation. It was found that the process of Notch translocation by Ex-4 was inhibited by pretreatment for 2 h with a γ-secretase inhibitor, L-685,458 (Shearman, et al., *Biochemistry*, 39:8698-8704, (2000)) (FIG. 5A), which also prevented the R-JAG-mediated increases and diminished Ex-4-mediated increases in IRS-2 (FIG. 10). The presence of presenilin-1, the active component of the γ-secretase complex (Li, et al., *Nature*, 405:689-694 (2000)), in β-cells was confirmed (FIG. 11), and the direct effect of Ex-4 on γ-secretase cleavage of the C-terminal end of Notch-1 from the membrane was measured. A cDNA encoding Gal4DNA-binding/VP16 transactivation (GVP), which is an immediate substrate for γ-secretase, was inserted into the C-terminus of the site 3 cleavage site of Notch to generate the Notch ΔE-GVP. Notch ΔE-GVP is cleaved from the membrane in a ligand independent manner and is translocated to the nucleus by virtue of the nuclear localisation signals in GVP. GVP specifically signals through a UAS-luciferase reporter gene via a strong transactivation domain and specific binding to a UAS promoter (Karlstroin, et al., *J Biol Chem*, 277:6763-6766 (2002)). It was found that Ex-4 increased the transcriptional activation of the UAS promoter at least 20-fold. This was greatly diminished by both H89 and L-685,458 (FIG. 5C). These findings reveal a previously unknown function of γ-secretase-mediated Notch cleavage in the insulinotropic response of β-cells to GLP-1R activation. Moreover, the data demonstrate that stimuli that increase cAMP induce Notch activation, and that PKA is necessary for activation of Notch by glucose and GLP-1.

Notch along with Mastermind is known to recruit RBP-Jκ to a transcriptional activation complex (Nam, et al., *J Biol Chem*, 278:21232-21239 (2003)). The other necessary co-activators in this complex are the histone acetyltransferases p300 and PCAF (Wallberg, et al., *Mol Cell Biol*, 22:7812-7819 (2002)). p300 is a non-DNA binding protein that is essential for transcriptional activation of genes, i.e., insulin, but requires chaperone transcription factors such as PDX-1 for binding to the insulin promoter (Mosley, et al., *Mol Endocrinol*, May 27 (Epub ahead of print) (2004) and Stanojevic, et al., *Endocrinology*, 145:2918-2928 (2004)). Therefore, p300 activation of target genes might be regulated by NICD/transcription factor complex.

During the fasted state β-cells probably have on-going low-level ligand/Notch interactions, but little or no NICD translocation because of low PKA activity, resulting in low γ-secretase activity. After eating, increasing levels of GLP-1 as well as glucose reach the islets, which increase cAMP-dependent PKA activity. Glucose alone probably influenced NICD translocation by providing the phosphates from ATP generation for phosphorylation of PKA substrates, even at basal activity (Takahashi, et al., *Proc Natl Acad Sci USA*, 96:760-765 (1999)). Part of the beneficial effects of GLP-1R agonists in the endocrine pancreas of rodents in diabetes and ageing (Wang, et al., *J Clin Invest*, 99:2883-2889 (1997)) may be due to their activation of the Notch-1 signalling pathway, which, in a manner analogous to muscle (Conboy, et al., *Science*, 302:1575-1577 (2003)), may become dysfunctional with age and Type-2 diabetes. Increasing signalling via the Notch pathways, not only by GLP-1R agonists, but also by Jagged-related peptides, can be a general mechanism to treat insulin-deficient states. Furthermore, the finding that Notch is activated by a hormone suggests an explanation for the context dependency of the effect of Notch on cell fate decisions.

Methods

Islet isolation, cell culture and treatments. Adult rat (Sprague-Dawley) and mouse (C57/BL6) islets were isolated by collagenase P digestion and cultured overnight in M199 medium (5 mM glucose). RIN 1046-38 β-cells were cultured as outlined previously (Wang, et al., *Endocrinology*, 142: 1820-1827 (2001)). Isolated human islets came from David Harlan, Transplant Section, NIDDK. Ex-4, GLP-1, CCK (all used at concentrations previously shown to cause maximum insulin release), Ex [9-39] and the γ-secretase inhibitor, L-685,458, were obtained from Bachem. H89 was from Calbiochem, insulin was from Sigma. The Jagged peptides, R-JAG CDDYYYGFGCNKFGRPRDD (SEQ ID NO:1), JAG-1 CDDYYYGFGCNKFCRPR (SEQ ID NO:2), and scrambled control peptide without agonist activity, sc-Jagged RCGPDCFDNYGRYKYCF (Nickoloff, et al., *Cell Death Differ*, 9842-855 (2002)) (SEQ ID NO:3), were synthesised by New England Peptide Inc.

Cell extracts, immunoblotting and RT-PCR. Cytosolic and nuclear cell extracts were prepared using the NE-PER Nuclear and Cytoplasmic Extraction Reagents (Pierce) in accordance with the manufacturer's instructions. Whole cell extracts were isolated as described (Wang, et al., *Endocrinology*, 142:1820-1827 (2001)). Cell extracts were separated by Tris-glycine (10%, 4-12%) PAGE (Invitrogen) and immunoblofted as described (Wang, et al., *Endocrinology*, 142:1820-1827 (2001)) using the following antibodies: rabbit anti-Notch1 (1:5,000), rabbit anti-IRS2 (1:1,000), both from Upstate Biotechnology, rabbit N-terminal anti-PDX-1 (1:10,000, from Joel Habener (Stanojevic, et al., *Endocrinology*, 145:2918-2928 (2004)). Total RNA was extracted using Triazol (Invitrogen) according to the manufacturer's instructions. RT-PCR was performed using the Qiagen OneStep RT-PCR kit. See Table 2 for primer sequences and annealing temperatures. Each target gene was amplified over 35 cycles.

TABLE 2

Sequence information for PCR primers

| Gene | Product Size (bp) | Upstream Primer | Downstream Primer | Annealing Temp (° C.) | Ref |
|---|---|---|---|---|---|
| hNotch1 | 428 | 5'-caggcaatccgaggactatg-3' (SEQ ID NO: 14) | 5'-caggcgtgttgttctcacag-3' (SEQ ID NO: 15) | 55 | 1 |
| hNotch2 | 529 | 5'-tgagtaggctccatccagtc-3' (SEQ ID NO: 16) | 5'-tggtgtcaggtagggatgct-3' (SEQ ID NO: 17) | 55 | 1 |
| hNotch3 | 485 | 5'-tcttgctgctggtcattctc-3' (SEQ ID NO: 18) | 5'-tgcctcatcctcttcagttg-3' (SEQ ID NO: 19) | 56 | 1 |
| hNotch4 | 472 | 5'-cactgagccaaggcatagac-3' (SEQ ID NO: 20) | 5'-atctccacctcacaccactg-3' (SEQ ID NO: 21) | 56 | 1 |
| mNotch1 | 246 | 5'-tgcctgtgcacaccattctgc-3' (SEQ ID NO: 22) | 5'-caatcagagatgttgaggtgc-3' (SEQ ID NO: 23) | 55 | 3 |
| mNotch2 | 279 | 5'-atgcaccatgacatcgttcg-3' (SEQ ID NO: 24) | 5'-gatagagtcactgagctctcg-3' (SEQ ID NO: 25) | 55 | 3 |
| mNotch3 | 359 | 5'-ttggtctgctcaatcctgtagc-3' (SEQ ID NO: 26) | 5'-tggcattggtagcagttgctg-3' (SEQ ID NO: 27) | 55 | 3 |
| mNotch4 | 297 | 5'-aagcgacacgtacgagtctgg-3' (SEQ ID NO: 28) | 5'-atagttgccagctacttgtgg-3' (SEQ ID NO: 29) | 55 | 3 |
| rNotch3 | 292 | 5'-accctgtgtgagcgaaacg-3' (SEQ ID NO: 30) | 5'-catcacgggcaaactccaaag-3' (SEQ ID NO: 31) | 55 | *1 |
| hJagged-1 | 227 | 5'-tcgctgtatctgtccacctg-3' (SEQ ID NO: 32) | 5'-agtcactggcacggttgtag-3' (SEQ ID NO: 33) | 56 | 2 |
| hJagged-2 | 600 | 5'-gattggcggctattactgtg-3' (SEQ ID NO: 34) | 5'-aggcagtcgtcaatgttctc-3' (SEQ ID NO: 35) | 56 | *2 |
| mJagged-1 | 249 | 5'-tgtgtgaagttggaagcatcc-3' (SEQ ID NO: 36) | 5'-atcttgagcttggtaatagcac-3' (SEQ ID NO: 37) | 55 | 3 |
| mJagged-2 | 262 | 5'-aaggacatactctaccagtgc-3' (SEQ ID NO: 38) | 5'-acgtccttggtacttctgacg-3' (SEQ ID NO: 39) | 55 | 3 |
| hDelta-1 | 382 | 5'-agacggagaccatgaacaac-3' (SEQ ID NO: 40) | 5'-tcctcggatatgacgtacac-3' (SEQ ID NO: 41) | 55 | 2 |
| hDelta-3 | 256 | 5'-gtgaatgccgatgcctagag-3' (SEQ ID NO: 42) | 5'-ggtccatctgcacatgtcac-3' (SEQ ID NO: 43) | 57 | 2 |

TABLE 2-continued

Sequence information for PCR primers

| Gene | Product Size (bp) | Upstream Primer | Downstream Primer | Annealing Temp (° C.) | Ref |
|------|-------------------|-----------------|-------------------|----------------------|-----|
| hDelta-4 | 620 | 5'-tgaccacttcggccactatg-3' (SEQ ID NO: 44) | 5'-agttggagccggtgaagttg-3' (SEQ ID NO: 45) | 55 | 2 |
| mDelta-1 | 244 | 5'-aagatggaagcgatgtgg-3' (SEQ ID NO: 46) | 5'-tcttcaaagcaactgtcc-3' (SEQ ID NO: 47) | 52 | 3 |
| mDelta-3 | 256 | 5'-ttgtggtgtccaatctctac-3' (SEQ ID NO: 48) | 5'-tggatctctgtgagttcgag-3' (SEQ ID NO: 49) | 55 | 3 |
| rDelta-4 | 318 | 5'-aacacaaaccagaagaaggagc-3' (SEQ ID NO: 50) | 5'-ggcgaccacaaacaggaag-3' (SEQ ID NO: 51) | 55 | *3 |
| rInsulin2 | 112 | 5'-tgtggttctcacttggtgga-3' (SEQ ID NO: 52) | 5'-gctccagttgtgccacttgt-3' (SEQ ID NO: 53) | 60 | *4 |
| rIRS2 | 157 | 5'-cctaagcagatcctgcaacc-3' (SEQ ID NO: 54) | 5'-attcgcatgtacccgctatc-3' (SEQ ID NO: 55) | 60 | *5 |
| hGAPDH | 226 | 5'-gaaggtgaaggtcggagtc-3' (SEQ ID NO: 56) | 5'-gaagatggtgatgggatttc-3' (SEQ ID NO: 57) | 56 | *6 |
| mGAPDH | 177 | 5'-tgcaccaccaactgcttag-3' (SEQ ID NO: 58) | 5'-ggatgcagggatgatgttc-3' (SEQ ID NO: 59) | 55 | *7 |

1. Nijjar, et al. Notch receptor expression in adult human liver: a possible role in bile duct formation and hepatic neovascularization. Hepatology 34: 1184-1192 (2001);
2. Nijjar, et al., Altered notch ligand expression in human liver disease. Am J Pathol 160: 1695-1703 (2002);
3. Kaneta, et al. A Role for Pref-1 and HES-1 in Thymocyte Development. J Immunol 164: 256-264 (2000).
*1 Rattus norvegicus Notch3 (Notch3) mRNA: NM_020087
*2 Homo sapiens delta-like-3 (Drosophila), transcript variant 1, mRNA: BC000218
*3 Rattus norvegicus similar to Notch ligand Delta-4 mRNA: XM_230472
*4 Rattus norvegicus insulin2 (Ins2) mRNA: NM_019130
*5 Rattus norvegicus insulin receptor substrate 2 (IRS2) mRNA: AF050159
*6 Homo sapiens glyceraldehyde-3-phosphate dehydrogenase mRNA: NM_002046
*7 Mus musculus glyceraldehyde-3-phosphate dehydrogenase mRNA: NM_001001303

Animal Protocols. Wild-type and GLP-1R −/− mice (Scrocchi, L. A. et al. *Nat. Med.*, 2:1254-1258 (1996)) were injected intraperitoneally with Ex-4 (1 nmol/kg) or glucose (1 g/kg) after overnight fast and their pancreata excised. Animal protocols were approved by the NIA Animal Care and Use Committee.

Insulin assays and cell turnover studies. Insulin secretion assays were performed and intracellular insulin was extracted as described (Wang, Y. et al., *J. Clin. Invest.*, 99:2883-2889 (1997)), followed by insulin quantification using an ELISA kit (Crystal Chem). Cells were treated for 8 h as indicated and pulsed with [$^3$H]thymidine (PerkinElmer Life Sciences) at 37° C., followed by lysis of the cells and [$^3$H] counting (He, et al., *J Biol Chem*, 278:27096-27104 (2003)).

Immunostaining. Antibodies used were the rabbit anti-Notch-1 (Upstate Biotechnology; 1:50) and goat anti-Jagged-1 (Santa Cruz; 1:200). Rat pancreata were fixed in 4% paraformaldehyde overnight, routinely processed and embedded in paraffin. Human prefixed pancreatic sections were obtained from Histology Control Systems. RIN cells were fixed in acid ethanol at −20° C. for 20 min.

Rat sections were stained with anti-Notch-1 using Zymed Histomouse BroadSpectrum, and human sections were stained with anti-Notch-1 on the Ventana Medical Systems Benchmark automated immunohistochemistry stainer using iView DAB detection and with anti-Jagged-1 using DAKO LSAB+ Peroxidase Universal detection. All sections were antigen-retrieved.

RIN cells were permeabilized in Triton-X (0.1%) on ice and blocked for 1 h at room temperature in 3% BSA and 0.1% Tween in PBS. They were incubated overnight at 4° C. with the primary antibody, washed in PBS and incubated with fluorescent labelled secondary antibody for 1 h, washed and mounted with fluorescence mounting medium (Vector Laboratories). Mouse sections (FIG. 9) for indirect immunofluorescence were antigen-retrieved, processed in the same manner as the cells and stained with anti-Notch-1. Indirect immunofluorescent staining was imaged using a Zeiss LSM-410 inverted microscope. AlexaFluor antibodies (Molecular Probes; Eugene, Oreg.) were excited with the 488-nm line of a krypton-argon laser and recorded at the presence of emission filter BP515-565 nm. The microscope objective was a Zeiss 63×NA 1.4 oil immersion and the confocal pinhole was set to obtain spatial resolution of 0.4 mm in the horizontal plane and 1 mm in the axial dimension.

Transfections and Luciferase assays. The rat insulin-I promoter linked to the luciferase reporter plasmid pGL3 (Ins-1-luc) was obtained from Michael Freemark (Fleenor and Freemark, *Endocrinology*, 142:2805-2810 (2001)), and both the Notch ΔE-GVP plasmid and UAS responsive reporter gene construct MH100 were from Johan Lundkvist (Karlstrom, et al., *J Biol Chem*, 277:6763-6766 (2002)). For the insulin reporter gene assay, RIN cells in 35 mm dishes were co-transfected with 0.8 μg ins-1-luc plasmid and 0.7 μg of pCMV-β-galactosidase using 8 μl of Polyfect (Qiagen). For the γ-secretase activity assay RIN cells in 12 well plates were co-transfected with 30 ng of pCMV-β-galactosidase, 200 ng of MH100, 100 ng Notch ΔE-GVP plasmids for each well using Lipofectamine PLUS (Invitrogen). The transfected cells were allowed to recover for 24-48 h in medium with serum and subsequently incubated in insulin secretion assay buffer (for the insulin promoter assay) or in medium without serum (for the γ-secretase assay) with or without Ex-4 and inhibitors. Ins-1-luc and Notch ΔE-GVP activities were measured using assay system kits from Promega according to the manufacturer's instructions using a Berthord LB 9501 luminometer. The luciferase values were normalized to β-galactosidase measured using the luminometer for lysates from 35 mm dishes and an ELISA plate reader (Spectra Max Plus, Molecular Devices) for lysates from 12 well plates.

Statistical Analysis. Data represent mean±SE. Differences between mean values for variables within individual experiments were compared statistically by ANOVA. Comparisons were performed using Graphpad Prism. P<0.05 was viewed as significant.

Example 2

Rat islets (80) were pre-incubated for 2 periods of 30 min in the glucose-free buffer in a 37° C. humidified air incubator. After a second 30-min period R-JAG (10 μM) was added in insulin secretion assay buffer with glucose (6 mM) and the peptide replenished every 6 hours for a further 18 hours. At the end of the experiment, islets were centrifuged and any residual medium removed and stored −20° C. for quantification of insulin released. The pellet was suspended in ice cold acid-ethanol (500 μl) and homogenized. After centrifugation of the homogenate (1,400 g, 4° C.) the supernatant was collected for measurement of intracellular insulin using the Rat insulin ELISA kit from Crystal Chem. Inc. (Chicago, Ill.). The pellet was lysed with 0.2 ml formic acid and saved at 20° C. for analysis of protein by the Bradford method (Bio-Rad Laboratories, Inc. Richmond, Calif.). A control condition with insulin secretion assay buffer containing just 6 mM glucose was used. Insulin values were normalized to protein content.

Reverse transcription. DNA-free RNA was isolated using the Triazol extraction method (Invitrogen; Carlsbad, Calif.) following the manufacturer's protocol. DNAse I treatment and inactivation, and reverse transcription reaction primed with random sequence oligonucleotides were performed using Ambion instruction manual and Cells-to-cDNA II kits components in the I-Cycler thermocycler from BioRad. As a control, a mock reverse transcription containing all RT reagents except the Reverse Transcriptase, which was substituted with water, was used.

Real Time PCR. Real time PCR reactions were performed using the ABI PRISM™ 7700 Sequence Detection Systems (Applied Biosystems; Valencia, Calif.) and the SYBER Green kit from Applied Biosystems. All PCR reactions were performed in triplicate using the SYBER Green master mix (12.5 μl) from Applied Biosystems, 1 μg of cDNA, 2.5 μl of each 0.5 μM primer and water for a 25 μl reaction. Cycling parameters for amplifications of target genes were (95° C. for 10 min, at 94° C. for 15 seconds, 60° C. for 1 min)×40 cycles. The target gene copy number in unknown samples was quantified by measuring the threshold cycle CT and by using the standard curve to determine the starting copy number. The β-actin gene was an endogenous control. Final results were expressed as n-fold differences relative to untreated controls. Primers used are shown in Table 3 below.

TABLE 3

| Sequence information for PCR primers | | | |
|---|---|---|---|
| rPDX-1 | F | 5'-CCAAAACCGTCGCATGAAGTG-3' | SEQ ID NO: 4 |
|  | R | 5'-CAGCTCGCCTGGTGGCTGT-3' | SEQ ID NO: 5 |
| rHES-1 | F | 5'-TACCCCAGCCAGTGTCAACA-3' | SEQ ID NO: 6 |
|  | R | 5'-TCCATGATAGGCTTTGATGACTTTC-3' | SEQ ID NO: 7 |
| rInsulin-1 | F | 5'-TGACCAGCTACAATCATAGACCA-3' | SEQ ID NO: 8 |
|  | R | 5'-CTCCAGTGCCAAGGTCTGA-3' | SEQ ID NO: 9 |
| rIRS-2 | F | 5'-GAGCCTTCAGTAGCCACAGG-3' | SEQ ID NO: 10 |
|  | R | 5'-CAGGCGTGGTTAGGGAGTAA-3' | SEQ ID NO: 11 |
| rβ-actin | F | 5'-CAGGGCATTGTAACCAACTG-3' | SEQ ID NO: 12 |
|  | R | 5'-AGGAAGGAAGGCTGGAAGAG-3' | SEQ ID NO: 13 |

Figure 12:
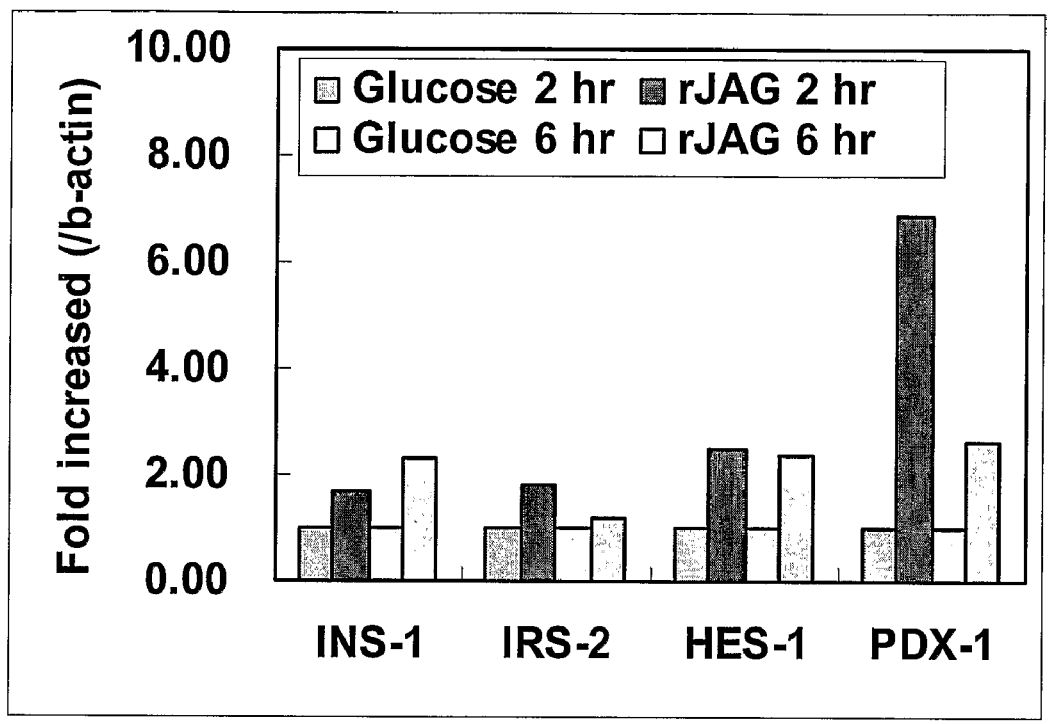
FIG. 12 shows real time PCR analysis of the insulin (INS-1), IRS-2, HES-1, and PDX-1 genes in rat islets in response to R-JAG shown in comparison to glucose at 2 hours and 6 hours of incubation. For the 6 hour incubation, R-JAG was replenished every 2 hours. Levels were normalized to β-actin.

The effects of the soluble ligands on adult islet cell function demonstrate that the soluble Notch ligand R-JAG increases insulin, PDX-1, and IRS-2 transcription over 2 and 6 hours (see FIG. 12 cellular insulin). This example also shows that this treatment leads to an increase in insulin synthesis as proven by an increase in intra-cellular insulin in rat islets, demonstrating the ability of the disclosed compositions and methods to improve β-cell function in a mammalian system as opposed to just in a cell line.

Figure 13:
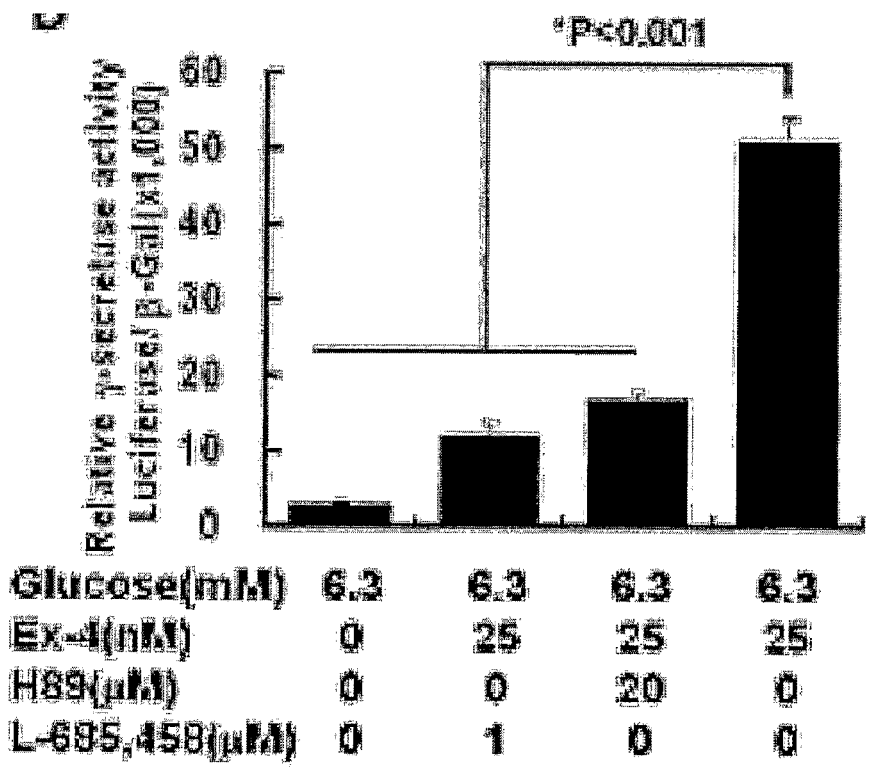
FIG. 13 shows Exendin-4 (Ex-4) causes NICD translocation in a PKA- and γ-secretase-dependent manner and processing of transfected Notch ΔE-GFP is sensitive to Ex-4. Ex-4 activated cleavage of Notch ΔE-GFP, which was blocked by H89 and L-685,458. Results are mean±SE, n=3.

Also demonstrated herein is that glucagon-like peptide-1 receptor (GLP-1-R) agonists activate Notch signaling by specifically activating γ-secretase. This was shown by measuring the direct effect of Ex-4 on γ-secretase cleavage of the C-terminal end of Notch-1 (NICD) from the membrane. A cDNA encoding Gal4DNA-binding/VP16 transactivation (GVP), which is an immediate substrate for γ-secretase, was inserted into the C-terminus of the site 3 cleavage site of Notch-1 to generate the Notch ΔE-GVP. Notch ΔE-GVP is cleaved from the membrane in a ligand-independent manner and is translocated to the nucleus by virtue of the nuclear localization signals in GVP. GVP specifically signals through a UAS-luciferase reporter gene via a strong transactivation domain and specific binding to a UAS promoter (Karlstrom, et al., A sensitive and quantitative assay for measuring cleavage of presenilin substrates. *J Biol Chem*, 277:6763-6766 (2002)). It was also found that Ex-4 increased the transcriptional activation of the UAS promoter at least 20-fold and this was greatly diminished by both H89 and L-685,458 (FIG. 13). These findings reveal a previously unknown function of γ-secretase-mediated Notch cleavage in the insulinotropic response of β-cells to GLP-1-R activation.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for identifying a pancreatic precursor cell comprising contacting a pancreatic cell sample with a marker that selectively binds a Notch receptor and detecting the bound marker, the cell that binds the marker being a pancreatic precursor cell.

2. The method of claim 1, wherein the pancreatic cell sample comprises a tissue sample.

3. The method of claim 1, wherein the Notch receptor comprises one or more Notch receptors chosen from Notch-1 receptor, Notch-2 receptor, Notch-3 receptor, and Notch-4 receptor.

4. The method of claim 1, wherein the marker comprises a Notch receptor ligand, a Notch-receptor binding fragment thereof, or both.

5. The method of claim 4, wherein the Notch receptor ligand comprises one or more Notch receptor ligands chosen from Jagged-1, Jagged-2, Delta-Like-1, Delta-Like-3, Delta-Like-4, and fragments thereof.

6. The method of claim 1, wherein the marker comprises an antibody to the Notch receptor.

7. The method of claim 1, wherein the marker is labeled with a detectable moiety.

8. A method for isolating a pancreatic precursor cell from a pancreatic cell sample, comprising identifying a cell that comprises a Notch receptor and separating the identified cell from the pancreatic cell sample, the separated cell being a pancreatic precursor cell.

9. The method of claim 8, wherein the pancreatic cell sample comprises pancreatic islet cells.

10. The method of claim 8, wherein the pancreatic cell sample comprises pancreatic extra-islet cells.

11. The method of claim 8, wherein the pancreatic cell sample comprises pancreatic islet cells and pancreatic extra-islet cells.

12. The method of claim 8, wherein the pancreatic cell sample comprises a sample from a subject with diabetes.

13. The method of claim 8, wherein the pancreatic cell sample comprises a sample from a human.

14. The method of claim 8, wherein the Notch receptor comprises one or more Notch receptors chosen from Notch-1 receptor, Notch-2 receptor, Notch-3 receptor, and Notch-4 receptor.

15. The method of claim 8, wherein the identifying step comprises contacting the pancreatic cell sample with a marker that selectively binds the Notch receptor and detecting the bound marker.

16. The method of claim 15, wherein the marker comprises a Notch receptor ligand, a Notch-receptor binding fragment thereof, or both.

17. The method of claim 15, wherein the marker comprises an antibody to the Notch receptor.

18. The method of claim 15, wherein the marker is labeled with a detectable moiety.

19. The method of claim 8, wherein the separating step comprises passing the pancreatic cell sample through a cell sorter that selects the identified cells.

20. The method of claim 8, wherein the separating step comprises passing the pancreatic cell sample through a column that selects the identified cells.

* * * * *